United States Patent
Mason et al.

(10) Patent No.: US 11,069,436 B2
(45) Date of Patent: Jul. 20, 2021

(54) SYSTEM AND METHOD FOR USE OF TELEMEDICINE-ENABLED REHABILITATIVE HARDWARE AND FOR ENCOURAGING REHABILITATIVE COMPLIANCE THROUGH PATIENT-BASED VIRTUAL SHARED SESSIONS WITH PATIENT-ENABLED MUTUAL ENCOURAGEMENT ACROSS SIMULATED SOCIAL NETWORKS

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM Technologies, Inc., Brookfield, CT (US)

( * ) Notice: Subject to any disclaimer, the term of this patent is extended or adjusted under 35 U.S.C. 154(b) by 0 days.

(21) Appl. No.: 17/147,990

(22) Filed: Jan. 13, 2021

(65) Prior Publication Data
US 2021/0134429 A1 May 6, 2021

Related U.S. Application Data

(63) Continuation-in-part of application No. 17/021,895, filed on Sep. 15, 2020.
(Continued)

(51) Int. Cl.
*G16H 10/60* (2018.01)
*G16H 20/30* (2018.01)
(Continued)

(52) U.S. Cl.
CPC ......... *G16H 20/30* (2018.01); *A63B 24/0062* (2013.01); *A63B 71/0622* (2013.01);
(Continued)

(58) Field of Classification Search
CPC ........ G16H 20/30; G16H 40/67; G16H 10/60; G16H 50/30; G16H 50/70; G16H 50/20;
(Continued)

(56) References Cited

U.S. PATENT DOCUMENTS

| 6,182,029 B1 | 1/2001 | Friedman |
| 6,413,190 B1 | 7/2002 | Wood et al. |

(Continued)

FOREIGN PATENT DOCUMENTS

| CA | 2698078 | 3/2010 |
| CN | 112603295 | 2/2003 |
| WO | 2019204876 | 4/2019 |

*Primary Examiner* — George Manuel
(74) *Attorney, Agent, or Firm* — Dickinson Wright, PLLC; Stephen A. Mason; Jonathan H. Harder

(57) ABSTRACT

In one embodiment, a computer-implemented system includes a treatment apparatus configured to be manipulated by a user while performing an exercise session, patient interfaces associated with users, and a server computing device configured to receive treatment data pertaining to the user, determine whether at least one characteristic of the user matches at least one second characteristic of a second user, where the second user belonging to a cohort. Responsive to determining the at least one characteristic of the user matches the at least one second characteristic of the second user, the server computing device is configured to assign the user to the cohort and select, via a trained machine learning model, a treatment plan for the user. Responsive to transmitting a signal to the patient interfaces of users in the
(Continued)

cohort, the server computing device enables the patient interfaces to establish the virtual shared session between the patient interfaces.

30 Claims, 18 Drawing Sheets

Related U.S. Application Data

(60) Provisional application No. 62/910,232, filed on Oct. 3, 2019.

(51) Int. Cl.
| | |
|---|---|
| *G16H 50/70* | (2018.01) |
| *G16H 50/20* | (2018.01) |
| *G16H 40/67* | (2018.01) |
| *G16H 80/00* | (2018.01) |
| *G16H 50/30* | (2018.01) |
| *A63B 24/00* | (2006.01) |
| *A63B 71/06* | (2006.01) |
| *A63B 22/00* | (2006.01) |
| *G06F 3/14* | (2006.01) |
| *A63B 22/06* | (2006.01) |

(52) U.S. Cl.
CPC .............. *G16H 10/60* (2018.01); *G16H 40/67* (2018.01); *G16H 50/20* (2018.01); *G16H 50/30* (2018.01); *G16H 50/70* (2018.01); *G16H 80/00* (2018.01); *A63B 22/0605* (2013.01); *A63B 2022/0094* (2013.01); *A63B 2024/0081* (2013.01); *A63B 2071/0625* (2013.01); *A63B 2071/0655* (2013.01); *A63B 2225/20* (2013.01); *G06F 3/1454* (2013.01)

(58) Field of Classification Search
CPC .......................... G16H 80/00; A63B 24/0062; A63B 71/0622; A63B 22/0605; A63B 2022/0094; A63B 2024/0081; A63B 2071/0625; A63B 2071/0655; A63B 2225/20; G06F 3/1454
See application file for complete search history.

(56) References Cited

U.S. PATENT DOCUMENTS

| | | | |
|---|---|---|---|
| 6,491,649 B1 | 12/2002 | Ombrellaro | |
| 7,169,085 B1 | 1/2007 | Killin et al. | |
| 7,209,886 B2 | 4/2007 | Kimmel | |
| 7,974,689 B2 | 7/2011 | Volpe et al. | |
| 8,751,264 B2 | 6/2014 | Beraja et al. | |
| 8,823,448 B1 | 9/2014 | Shen | |
| 9,311,789 B1 | 4/2016 | Gwin | |
| 9,919,198 B2 | 3/2018 | Romeo et al. | |
| 9,939,784 B1 | 4/2018 | Berardinelli | |
| 10,130,298 B2 | 11/2018 | Mokaya et al. | |
| 10,424,033 B2 | 9/2019 | Romeo | |
| 2003/0036683 A1 | 2/2003 | Kehr et al. | |
| 2003/0109814 A1 | 6/2003 | Rummerfield | |
| 2006/0064329 A1 | 3/2006 | Abolfathi et al. | |
| 2009/0011907 A1 | 1/2009 | Radow et al. | |
| 2009/0070138 A1 | 3/2009 | Langheier et al. | |
| 2010/0268304 A1 | 10/2010 | Matos | |
| 2011/0172059 A1 | 7/2011 | Watterson et al. | |
| 2011/0218814 A1 | 9/2011 | Coats | |
| 2012/0065987 A1 | 3/2012 | Farooq et al. | |
| 2012/0190502 A1 | 7/2012 | Paulus et al. | |
| 2012/0310667 A1 | 12/2012 | Altman et al. | |
| 2013/0123071 A1 | 5/2013 | Rhea | |
| 2013/0123667 A1 | 5/2013 | Komatireddy et al. | |
| 2013/0296987 A1 | 11/2013 | Rogers et al. | |
| 2014/0006042 A1 | 1/2014 | Keefe et al. | |
| 2014/0188009 A1 | 7/2014 | Lange et al. | |
| 2014/0194250 A1 | 7/2014 | Reich et al. | |
| 2014/0257837 A1 | 9/2014 | Walker et al. | |
| 2014/0322686 A1 | 10/2014 | Kang | |
| 2015/0088544 A1 | 3/2015 | Goldberg | |
| 2015/0161331 A1 | 6/2015 | Oleynik | |
| 2015/0339442 A1 | 11/2015 | Oleynik | |
| 2016/0140319 A1 | 5/2016 | Stark et al. | |
| 2016/0166881 A1 | 6/2016 | Ridgel et al. | |
| 2016/0275259 A1 | 9/2016 | Nolan et al. | |
| 2016/0302721 A1 | 10/2016 | Wiedenhoefer et al. | |
| 2017/0004260 A1 | 1/2017 | Moturu et al. | |
| 2017/0143261 A1 | 5/2017 | Wiedenhoefer et al. | |
| 2017/0147789 A1 | 5/2017 | Wiedenhoefer et al. | |
| 2017/0181698 A1 | 6/2017 | Wiedenhoefer et al. | |
| 2017/0243028 A1 | 8/2017 | LaFever et al. | |
| 2017/0278209 A1* | 9/2017 | Olsen | G16H 10/60 |
| 2017/0300654 A1 | 10/2017 | Stein et al. | |
| 2017/0329917 A1 | 11/2017 | McRaith et al. | |
| 2017/0344773 A1 | 11/2017 | Duffy et al. | |
| 2017/0360586 A1 | 12/2017 | Dempers et al. | |
| 2018/0052962 A1 | 2/2018 | Van Der Koijk et al. | |
| 2018/0085615 A1 | 3/2018 | Astolfi et al. | |
| 2018/0102190 A1 | 4/2018 | Hogue et al. | |
| 2018/0240552 A1 | 8/2018 | Tuyl et al. | |
| 2018/0271432 A1 | 9/2018 | Auchinleck et al. | |
| 2018/0280784 A1 | 10/2018 | Romeo et al. | |
| 2018/0330824 A1 | 11/2018 | Athey et al. | |
| 2019/0019578 A1 | 1/2019 | Vaccaro | |
| 2019/0066832 A1 | 2/2019 | Kang et al. | |
| 2019/0167988 A1 | 6/2019 | Shahriari et al. | |
| 2020/0143922 A1 | 5/2020 | Chekroud et al. | |
| 2020/0151595 A1 | 5/2020 | Jayalath et al. | |
| 2020/0152339 A1 | 5/2020 | Pulitzer et al. | |
| 2020/0160198 A1 | 5/2020 | Reeves et al. | |
| 2020/0176098 A1 | 6/2020 | Lucas et al. | |
| 2020/0293712 A1 | 9/2020 | Potts et al. | |
| 2020/0401224 A1 | 12/2020 | Cotton | |

* cited by examiner

SYSTEM AND METHOD FOR USE OF TELEMEDICINE-ENABLED REHABILITATIVE HARDWARE AND FOR ENCOURAGING REHABILITATIVE COMPLIANCE THROUGH PATIENT-BASED VIRTUAL SHARED SESSIONS WITH PATIENT-ENABLED MUTUAL ENCOURAGEMENT ACROSS SIMULATED SOCIAL NETWORKS

CROSS-REFERENCES TO RELATED APPLICATIONS

This application is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes.

BACKGROUND

Remote medical assistance, also referred to, inter alia, as remote medicine, telemedicine, telemed, telmed, tel-med, or telehealth, is an at least two-way communication between a medical professional or healthcare professional, such as a physician or a physical therapist, and a patient using audio and/or audiovisual and/or other sensorial or perceptive (e.g., gesture-based, tactile, gustatory, haptic, pressure-sensing-based or electromagnetic (e.g., neurostimulation)) communications (e.g., via a computer, a smartphone, or a tablet). In some embodiments, gesture recognition, gesture control, touchless user interfaces (TUIs), kinetic user interfaces (KUIs), tangible user interfaces, wired gloves, depth-aware cameras, stereo cameras, and/or gesture-based controllers may be used. Telemedicine may aid a patient in performing various aspects of a rehabilitation regimen for a body part. The patient may use a patient interface in communication with an assistant interface for receiving the remote medical assistance via audio and/or audiovisual communications. Further, virtual shared sessions may include streaming multimedia feeds between one or more patient interfaces and/or one or more assistant interfaces. Any reference herein to any particular sensorial modality shall be understood to include and to disclose by implication a different one or more sensory modalities.

SUMMARY

In one embodiment, a computer-implemented system includes a treatment apparatus configured to be manipulated by a user while performing an exercise session, patient interfaces associated with users, and a server computing device configured to receive treatment data pertaining to the user, and the computer-implemented system is configured to determine whether at least one characteristic of the user matches at least one second characteristic of a second user, where the second user belongs to a cohort. Responsive to determining that the at least one characteristic of the user matches the at least one second characteristic of the second user, the server computing device may be configured to assign the user to the cohort and select, via a trained machine learning model, a treatment plan for the user. Responsive to transmitting a signal to the patient interfaces of users in the cohort, the server computing device may enable the patient interfaces to establish the virtual shared session between the patient interfaces.

In one embodiment, a computer-implemented method includes receiving a plurality of first characteristics pertaining to a plurality of users and initiating a virtual shared session on a set of computing devices associated with a set of users. The virtual shared session includes at least a set of multimedia feeds, and each multimedia feed of the set of multimedia feeds is associated with one or more of the users of the set of users. During the virtual shared session, the method also includes presenting a first layout comprising the plurality of multimedia feeds, the plurality of first characteristics, or some combination thereof.

In one embodiment, a computer-implemented method is disclosed for configuring a virtual shared treatment session to encourage a user compliance with a treatment plan. The method includes receiving treatment data pertaining to the user, wherein the treatment data comprises one or more characteristics of the user. The method includes determining whether at least one characteristic of the one or more characteristics of the user matches at least one second characteristic of one or more second characteristics of a second user, wherein the second user belongs to a cohort. Responsive to determining the at least one characteristic of the first user matches the at least one second characteristic of the second user, the method also includes assigning the first user to the cohort and selecting, via an artificial intelligence engine, a treatment plan for the first user. Responsive to transmitting a signal to computing devices of users in the cohort, the method also includes enabling the computing devices to establish the virtual shared session between the computing devices. The method also includes enabling the virtual shared session between the computing devices of the users in the cohort.

In one embodiment, a system includes a memory that stores instructions and a processing device communicatively coupled to the memory. The processing device executes the instructions to perform any of the methods, operations, or steps described herein.

In one embodiment, a tangible, non-transitory computer-readable medium stores instructions that, when executed, cause a processing device to perform any of the methods, operations, or steps described herein.

BRIEF DESCRIPTION OF THE DRAWINGS

For a detailed description of example embodiments, reference will now be made to the accompanying drawings in which.

NOTATION AND NOMENCLATURE

Figure 1:
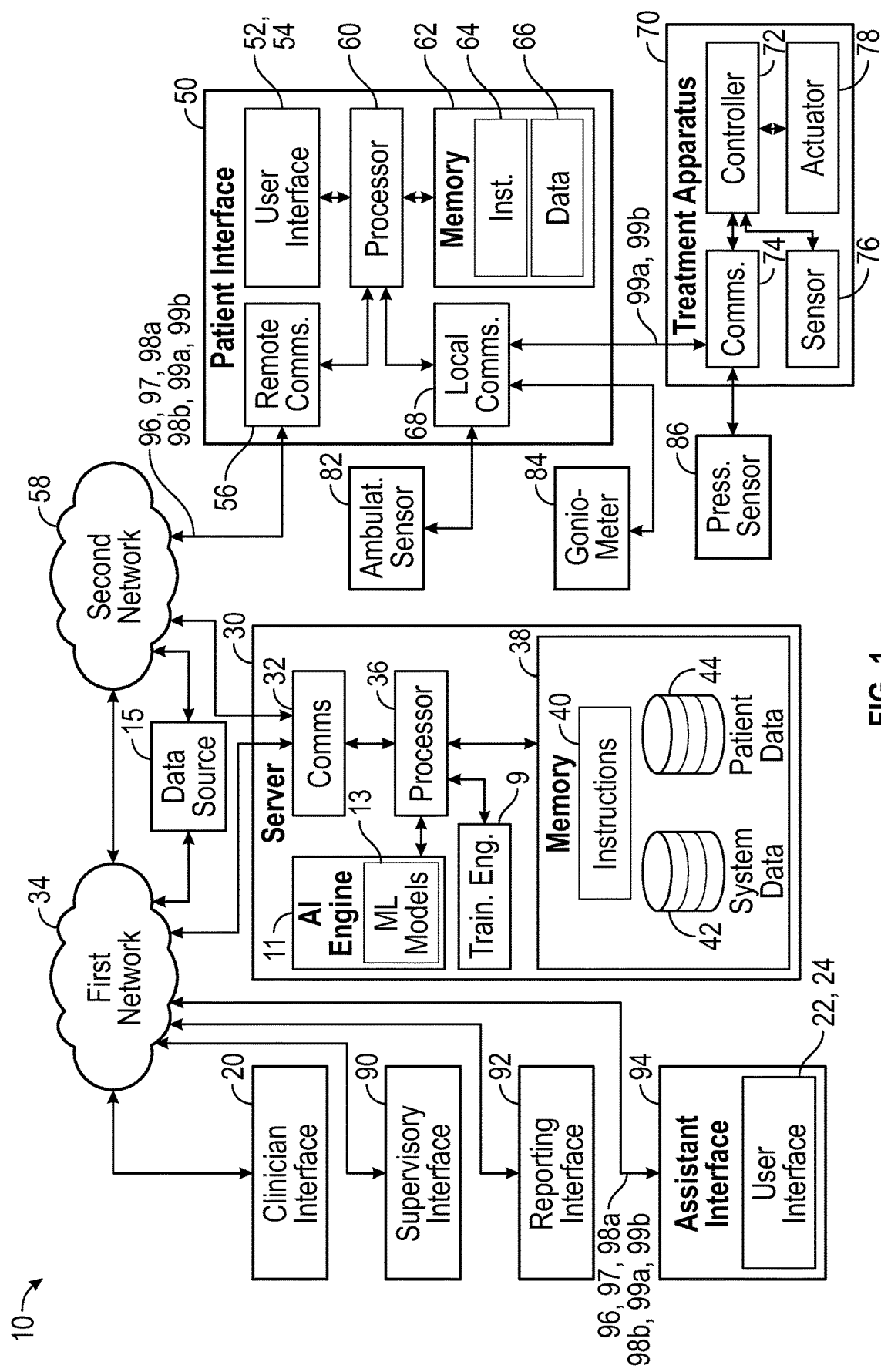
FIG. 1 shows a block diagram of an embodiment of a computer implemented system for managing a treatment plan according to the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols or exercise regimens, and each treatment protocol or exercise regimen includes one or more treatment sessions or one or more exercise sessions. Each treatment session or exercise session comprises one or more session periods or exercise periods, with each session period or exercise period including at least one exercise for treating the body part of the patient. Any suitable exercise (e.g., muscular, weight lifting, cardiovascular, therapeutic, neuromuscular, neurocognitive, meditating, yoga, stretching, etc.) may be included in a session period or an exercise period. For example, a treatment plan for post-operative rehabilitation after a knee surgery may include an initial treatment protocol or exercise regimen with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The terms telemedicine, telehealth, telemed, teletherapeutic, etc. may be used interchangeably herein.

The term "optimal treatment plan" may refer to optimizing a treatment plan based on a certain parameter or factors or combinations of more than one parameter or factor, such as, but not limited to, a measure of benefit which one or more exercise regimens provide to users, one or more probabilities of users complying with one or more exercise regimens, an amount, quality or other measure of sleep associated with the user, information pertaining to a diet of the user, information pertaining to an eating schedule of the user, information pertaining to an age of the user, information pertaining to a sex of the user, information pertaining to a gender of the user, an indication of a mental state of the user, information pertaining to a genetic condition of the user, information pertaining to a disease state of the user, an indication of an energy level of the user, information pertaining to a microbiome from one or more locations on or in the user (e.g., skin, scalp, digestive tract, vascular system, etc.), or some combination thereof.

Real-time may refer to less than or equal to 2 seconds. Near real-time may refer to any interaction of a sufficiently short time to enable two individuals to engage in a dialogue via such user interface, and will preferably but not determinatively be less than 10 seconds but greater than 2 seconds.

Any of the systems and methods described in this disclosure may be used in connection with rehabilitation. Rehabilitation may be directed at cardiac rehabilitation, rehabilitation from stroke, multiple sclerosis, Parkinson's disease, myasthenia gravis, Alzheimer's disease, any other neurodegenerative or neuromuscular disease, a brain injury, a spinal cord injury, a spinal cord disease, a joint injury, a joint disease, post-surgical recovery, or the like. Rehabilitation can further involve muscular contraction in order to improve blood flow and lymphatic flow, engage the brain and nervous system to control and affect a traumatized area to increase the speed of healing, reverse or reduce pain (including arthralgias and myalgias), reverse or reduce stiffness, recover range of motion, encourage cardiovascular engagement to stimulate the release of pain-blocking hormones or to encourage highly oxygenated blood flow to aid in an overall feeling of well-being. Rehabilitation may be provided for individuals of average weight in reasonably good physical condition having no substantial deformities, as well as for individuals more typically in need of rehabilitation, such as those who are elderly, obese, subject to disease processes, injured and/or who have a severely limited range of motion. Unless expressly stated otherwise, is to be understood that rehabilitation includes prehabilitation (also referred to as "pre-habilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through, dissecting and/or harming numerous muscles and muscle groups in or about, without limitation, the skull or face, the abdomen, the ribs and/or the thoracic cavity, as well as in or about all joints and appendages. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. Performance of the one or more sets of exercises may be required in order to qualify for an elective surgery, such as a knee replacement. The patient may prepare an area of his or her body for the surgical procedure by performing the one or more sets of exercises, thereby strengthening muscle groups, improving existing muscle memory, reducing pain, reducing stiffness, establishing new muscle memory, enhancing mobility (i.e., improve range of motion), improving blood flow, and/or the like.

The phrase, and all permutations of the phrase, "respective measure of benefit with which one or more exercise regimens may provide the user" (e.g., "measure of benefit," "respective measures of benefit," "measures of benefit," "measure of exercise regimen benefit," "exercise regimen benefit measurement," etc.) may refer to one or more measures of benefit with which one or more exercise regimens may provide the user.

The term "user" may refer to a patient, a patient's family member or assistant, a healthcare professional, a volunteer, a participant, a trainer, a member, a person, a coach, a player, or the like.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining a treatment plan for a patient having certain characteristics (e.g., vital-sign or other measurements; performance; demographic; geographic; diagnostic; measurement- or test-based; medically historic; etiologic; cohort-associative; differentially diagnostic; surgical, physically therapeutic, microbiome, pharmacologic and other treatment(s) recommended; arterial blood gas and/or oxygenation levels or percentages; glucose levels; insulin levels; psychographics; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, or some combination thereof. The measurement information may include, e.g., a vital sign, a respiration rate, a heartrate, a temperature, a blood pressure, arterial blood gas and/or oxygenation levels or percentages, or some combination thereof. It may be desirable to process the characteristics of a multitude of patients, the treatment plans performed for those patients, and the results of the treatment plans for those patients.

Further, another technical problem may involve distally treating, via a computing device during a telemedicine or telehealth session, a patient from a location different than a location at which the patient is located. An additional technical problem is controlling or enabling the control of, from the different location, a treatment apparatus used by the patient at the location at which the patient is located. Oftentimes, when a patient undergoes rehabilitative surgery (e.g., knee surgery), a physical therapist or other healthcare professional may prescribe a treatment apparatus to the patient to use to perform a treatment protocol at their residence or any mobile location or temporary domicile. A healthcare professional may refer to a doctor, physician assistant, nurse, chiropractor, dentist, physical therapist, acupuncturist, physical trainer, psychologist, psychotherapist, life coach, instructor, or the like. A healthcare professional may refer to any person with a credential, license, degree, or the like in the field of medicine, physical therapy, rehabilitation, psychology, biology, or the like.

Since the physical therapist or other healthcare professional is located in a different location from the patient and the treatment apparatus, it may be technically challenging for the physical therapist or other healthcare professional to monitor the patient's actual progress (as opposed to relying on the patient's word about their progress) using the treatment apparatus, modify the treatment plan according to the patient's progress, adapt the treatment apparatus to the personal characteristics of the patient as the patient performs the treatment plan, and the like.

Accordingly, some embodiments of the present disclosure pertain to using artificial intelligence and/or machine learning to dynamically and distally control (e.g., via a server) a treatment apparatus based on the assignment during an adaptive telemedical session. In some embodiments, numerous treatment apparatuses may be provided to patients. The treatment apparatuses may be used by the patients to perform treatment plans in their residences, at a gym, at a rehabilitative center, at a hospital, at a work site, or any suitable location, including permanent or temporary domiciles. In some embodiments, the treatment apparatuses may be communicatively coupled to a server. Characteristics of the patients may be collected before, during, and/or after the patients perform the treatment plans. For example, the personal information, the performance information, and the measurement information may be collected before, during, and/or after the person performs the treatment plans. The results (e.g., improved performance or decreased performance) of performing each exercise may be collected from the treatment apparatus throughout the treatment plan and after the treatment plan is performed. The parameters, settings, configurations, etc. (e.g., position of pedal, amount of resistance, etc.) of the treatment apparatus may be collected before, during, and/or after the treatment plan is performed.

Each characteristic of the patient, each result, and each parameter, setting, configuration, etc. may be timestamped and may be correlated with a particular step in the treatment plan. Such a technique may enable determining which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment apparatuses and/or any suitable computing device (e.g., computing devices where personal information is entered, such as a clinician interface or patient interface) over time as the patients use the treatment apparatuses to perform the various treatment plans. The data that may be collected may include the characteristics of the patients, the treatment plans performed by the patients, and the results of the treatment plans. Further, the data may include characteristics of the treatment apparatus. The characteristics of the treatment apparatus may include a make (e.g., identity of entity that designed, manufactured, etc. the treatment apparatus 70) of the treatment apparatus 70, a model (e.g., model number or other identifier of the model) of the treatment apparatus 70, a year (e.g., year the treatment apparatus was manufactured) of the treatment apparatus 70, operational parameters (e.g., engine temperature during operation, a respective status of each of one or more sensors included in or associated with the treatment apparatus 70, vibration measurements of the treatment apparatus 70 in operation, measurements of static and/or dynamic forces exerted internally or externally on the treatment apparatus 70, etc.) of the treatment apparatus 70, settings (e.g., range of motion setting, speed setting, required pedal force setting, etc.) of the treatment apparatus 70, and the like. The data collected from the treatment apparatuses, computing devices, characteristics of the user, characteristics of the treatment apparatus, and the like may be collectively referred to as "treatment data" herein.

In some embodiments, the data may be processed to group certain users into cohorts. The users may be grouped by users having certain or selected similar characteristics, treatment plans, and results of performing the treatment plans. For example, athletic users having no medical conditions who perform a treatment plan (e.g., use the treatment apparatus for 30 minutes a day 5 times a week for 3 weeks) and who fully recover may be grouped into a first cohort. Older users who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment apparatus while the new patient uses the treatment apparatus to perform the treatment plan.

As may be appreciated, the characteristics of the new patient may change as the new patient uses the treatment apparatus to perform the treatment plan. For example, the performance of the patient may improve quicker than expected for users in the cohort to which the new patient is currently assigned. Accordingly, the machine learning models may be trained to dynamically reassign, based on the changed characteristics, the new patient to a different cohort that includes users having characteristics similar to the now-changed characteristics as the new patient. For example, a clinically obese patient may lose weight and no longer meet the weight criterion for the initial cohort, result in the patient's being reassigned to a different cohort with a different weight criterion. A different treatment plan may be selected for the new patient, and the treatment apparatus may be controlled, distally and based on the different treatment plan, the treatment apparatus while the new patient uses the treatment apparatus to perform the treatment plan. Such techniques may provide the technical solution of distally controlling a treatment apparatus. Further, the techniques may lead to faster recovery times and/or better results for the patients because the treatment plan that most accurately fits their characteristics is selected and implemented, in real-time, at any given moment. Real-time may refer to less than or equal to 2 seconds. Near real-time may refer to any interaction of a sufficiently short time to enable two individuals to engage in a dialogue via such user interface, and will generally be less than 10 seconds but greater than 2 seconds. As described herein, the term "results" may refer to medical results or medical outcomes. Results and outcomes may refer to responses to medical actions.

In some embodiments, the artificial intelligence engine may receive treatment data pertaining to the user. The artificial intelligence engine may determine, via one or more trained machine learning models, a respective measure of benefit which one or more exercise regimens provide the user. The artificial intelligence engine may determine the measure of benefit based on the treatment data. The artificial intelligence engine may determine, via the one or more trained machine learning models, one or more probabilities of the user complying with the one or more exercise regimens. Further, the artificial intelligence engine may generate, based on the one or more probabilities and the respective measure of benefit which the one or more exercise regimens provide the user, a treatment plan that is transmitted to a computing device. The treatment plan may be used to distally control the treatment apparatus as the user uses the treatment apparatus to perform the one or more exercises included in the treatment plan.

In some embodiments, the treatment plans may be presented, during a telemedicine or telehealth session, to a healthcare professional. The healthcare professional may select a particular treatment plan for the patient to cause that treatment plan to be transmitted to the patient and/or to control, based on the treatment plan, the treatment apparatus. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment apparatus. In such cases, the recommended treatment plans and/or excluded treatment plans may be presented simultaneously with a video of the patient in real-time or near real-time during a telemedicine or telehealth session on a user interface of a computing device of a healthcare professional. The video may also be accompanied by audio, text and other multimedia information.

Presenting the treatment plans generated by the artificial intelligence engine concurrently with a presentation of the patient video may provide an enhanced user interface because the healthcare professional may continue to visually and/or otherwise communicate with the patient while also reviewing the treatment plans on the same user interface. The enhanced user interface may improve the healthcare professional's experience using the computing device and may encourage the healthcare professional to reuse the user interface. Such a technique may also reduce computing resources (e.g., processing, memory, network) because the healthcare professional does not have to switch to another user interface screen to enter a query for a treatment plan to recommend based on the characteristics of the patient. The artificial intelligence engine provides, dynamically on the fly, the treatment plans and excluded treatment plans.

In some embodiments, the treatment plan may be modified by a healthcare professional. For example, certain procedures may be added, modified or removed. In the telehealth scenario, there are certain procedures that may not be performed due to the distal nature of a healthcare professional using a computing device in a different physical location than a patient.

A technical problem may relate to the information pertaining to the patient's medical condition being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). That is, some sources used by various healthcare professional entities may be installed on their local computing devices and, additionally and/or alternatively, may use proprietary formats. Accordingly, some embodiments of the present disclosure may use an API to obtain, via interfaces exposed by APIs used by the sources, the formats used by the sources. In some embodiments, when information is received from the sources, the API may map and convert the format used by the sources to a standardized (i.e., canonical) format, language and/or encoding ("format" as used herein will be inclusive of all of these terms) used by the artificial intelligence engine. Further, the information converted to the standardized format used by the artificial intelligence engine may be stored in a database accessed by the artificial intelligence engine when the artificial intelligence engine is performing any of the techniques disclosed herein. Using the information converted to a standardized format may enable a more accurate determination of the procedures to perform for the patient.

The various embodiments disclosed herein may provide a technical solution to the technical problem pertaining to the patient's medical condition information being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). The information may be converted from the format used by the sources to the standardized format used by the artificial intelligence engine. Further, the information converted to the standardized format used by the artificial intelligence engine may be stored in a database accessed by the artificial intelligence engine when performing any of the techniques disclosed herein. The standardized information may enable generating optimal treatment plans, where the generating is based on treatment plans associated with the standardized information. The optimal treatment plans may be provided in a standardized format that can be processed by various applications (e.g., telehealth) executing on various computing devices of healthcare professionals and/or patients.

A technical problem may include a challenge of generating treatment plans for users, such treatment plans comprising exercises that balance a measure of benefit which the exercise regimens provide to the user and the probability the user complies with the exercises (or the distinct probabilities the user complies with each of the one or more exercises). By selecting exercises having higher compliance probabilities for the user, more efficient treatment plans may be generated, and these may enable less frequent use of the treatment apparatus and therefore extend the lifetime or time between recommended maintenance of or needed repairs to the treatment apparatus. For example, if the user consistently quits a certain exercise but yet attempts to perform the exercise multiple times thereafter, the treatment apparatus may be used more times, and therefore suffer more "wear-and-tear" than if the user fully complies with the exercise regimen the first time. In some embodiments, a technical solution may include using trained machine learning models to generate treatment plans based on the measure of benefit exercise regimens provide users and the probabilities of the users associated with complying with the exercise regimens, such inclusion thereby leading to more time-efficient, cost-efficient, and maintenance-efficient use of the treatment apparatus.

In some embodiments, the treatment apparatus may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare professional may adapt, remotely during a telemedicine session, the treatment apparatus to the needs of the patient by causing a control instruction to be transmitted from a server to treatment apparatus. Such adaptive nature may improve the results of recovery for a patient, furthering the goals of personalized medicine, and enabling personalization of the treatment plan on a per-individual basis.

FIG. 1 shows a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients.

The system data store 42 may be configured to store optimal treatment plans generated based on one or more probabilities of users associated with complying with the exercise regimens, and the measure of benefit with which one or more exercise regimens provide the user. The system data store 42 may hold data pertaining to one or more exercises (e.g., a type of exercise, which body part the exercise affects, a duration of the exercise, which treatment apparatus to use to perform the exercise, repetitions of the exercise to perform, etc.). When any of the techniques described herein are being performed, or prior to or thereafter such performance, any of the data stored in the system data store 42 may be accessed by an artificial intelligence engine 11.

The server 30 may also be configured to store data regarding performance by a patient in following a treatment plan. For example, the memory 38 includes a patient data store 44 configured to hold patient data, such as data pertaining to the one or more patients, including data representing each patient's performance within the treatment plan. The patient data store 44 may hold treatment data pertaining to users over time, such that historical treatment data is accumulated in the patient data store 44. The patient data store 44 may hold data pertaining to measures of benefit one or more exercises provide to users, probabilities of the users complying with the exercise regimens, and the like. The exercise regimens may include any suitable number of exercises (e.g., shoulder raises, squats, cardiovascular exercises, sit-ups, curls, etc.) to be performed by the user. When any of the techniques described herein are being performed, or prior to or thereafter such performance, any of the data stored in the patient data store 44 may be accessed by an artificial intelligence engine 11.

In addition, the determination or identification of: the characteristics (e.g., personal, performance, measurement, etc.) of the users, the treatment plans followed by the users, the measure of benefits which exercise regimens provide to the users, the probabilities of the users associated with complying with exercise regimens, the level of compliance with the treatment plans (e.g., the user completed 4 out of 5 exercises in the treatment plans, the user completed 80% of an exercise in the treatment plan, etc.), and the results of the treatment plans may use correlations and other statistical or probabilistic measures to enable the partitioning of or to partition the treatment plans into different patient cohort-equivalent databases in the patient data store 44. For example, the data for a first cohort of first patients having a first determined measure of benefit provided by exercise regimens, a first determined probability of the user associated with complying with exercise regimens, a first similar injury, a first similar medical condition, a first similar medical procedure performed, a first treatment plan followed by the first patient, and/or a first result of the treatment plan, may be stored in a first patient database. The data for a second cohort of second patients having a second determined measure of benefit provided by exercise regimens, a second determined probability of the user associated with complying with exercise regimens, a second similar injury, a second similar medical condition, a second similar medical procedure performed, a second treatment plan followed by the second patient, and/or a second result of the treatment plan may be stored in a second patient database. Any single characteristic, any combination of characteristics, or any measures calculation therefrom or thereupon may be used to separate the patients into cohorts. In some embodiments, the different cohorts of patients may be stored in different partitions or volumes of the same database. There is no specific limit to the number of different cohorts of patients allowed, other than as limited by mathematical combinatoric and/or partition theory.

This measure of exercise benefit data, user compliance probability data, characteristic data, treatment plan data, and results data may be obtained from numerous treatment apparatuses and/or computing devices over time and stored in the database 44. The measure of exercise benefit data, user compliance probability data, characteristic data, treatment plan data, and results data may be correlated in the patient-cohort databases in the patient data store 44. The characteristics of the users may include personal information, performance information, and/or measurement information.

In addition to the historical treatment data, measure of exercise benefit data, and/or user compliance probability data about other users stored in the patient cohort-equivalent databases, real-time or near-real-time information based on the current patient's treatment data, measure of exercise benefit data, and/or user compliance probability data about a current patient being treated may be stored in an appropriate patient cohort-equivalent database. The treatment data, measure of exercise benefit data, and/or user compliance probability data of the patient may be determined to match or be similar to the treatment data, measure of exercise benefit data, and/or user compliance probability data of another person in a particular cohort (e.g., a first cohort "A", a second cohort "B" or a third cohort "C", etc.) and the patient may be assigned to the selected or associated cohort.

In some embodiments, the server 30 may execute the artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign users to certain cohorts based on their treatment data, generate treatment plans using real-time and historical data correlations involving patient cohort-equivalents, and control a treatment apparatus 70, among other things. The machine learning models 13 may be trained to generate, based on one or more probabilities of the user complying with one or more exercise regimens and/or a respective measure of benefit one or more exercise regimens provide the user, a treatment plan at least a subset of the one or more exercises for the user to perform. The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based or a real-time software platform, and it may include privacy software or protocols, and/or security software or protocols.

To train the one or more machine learning models 13, the training engine 9 may use a training data set of a corpus of information (e.g., treatment data, measures of benefits of exercises provide to users, probabilities of users complying with the one or more exercise regimens, characteristic data, vital sign data, user performance data, compliance data, therapy data, ratings data etc.) pertaining to users who performed treatment plans using the treatment apparatus 70, the details (e.g., treatment protocol including exercises, amount of time to perform the exercises, instructions for the patient to follow, how often to perform the exercises, a schedule of exercises, parameters/configurations/settings of the treatment apparatus 70 throughout each step of the treatment plan, etc.) of the treatment plans performed by the users using the treatment apparatus 70, and/or the results of the treatment plans performed by the users, etc.

The one or more machine learning models 13 may be trained to match patterns of treatment data of a user with treatment data of other users assigned to a particular cohort. The term "match" may refer to an exact match, a correlative match, a substantial match, a probabilistic match, etc. The one or more machine learning models 13 may be trained to receive the treatment data of a patient as input, map the treatment data to the treatment data of users assigned to a cohort, and determine a respective measure of benefit one or more exercise regimens provide to the user based on the measures of benefit the exercises provided to the users assigned to the cohort. The one or more machine learning models 13 may be trained to receive the treatment data of a patient as input, map the treatment data to treatment data of users assigned to a cohort, and determine one or more probabilities of the user associated with complying with the one or more exercise regimens based on the probabilities of the users in the cohort associated with complying with the one or more exercise regimens.

The one or more machine learning models 13 may also be trained to receive various input (e.g., the respective measure of benefit which one or more exercise regimens provide the user; the one or more probabilities of the user complying with the one or more exercise regimens; an amount, quality or other measure of sleep associated with the user; information pertaining to a diet of the user, information pertaining to an eating schedule of the user; information pertaining to an age of the user, information pertaining to a sex of the user; information pertaining to a gender of the user; an indication of a mental state of the user; information pertaining to a genetic condition of the user; information pertaining to a disease state of the user; an indication of an energy level of the user; or some combination thereof), and to output a generated treatment plan for the patient.

The one or more machine learning models 13 may also be trained to receive various input (e.g., characteristics (e.g., user identity, ratings (a performance rating, a fitness rating, a rehabilitation rating, a prehabilitation rating, an exercise rating, an athleticism rating, a competition level rating, a credit rating, a personality assessment, a personality inventory, or some combination thereof), statistics (pedaling speed, range of motion, force exerted on pedals), measurement data, performance data, personal data, compliance data, therapy data, etc.), and to output a generated layout of multimedia feeds and/or user characteristics, to transmit a notification (motivational message, incentive offer) to a computing device of a user, to select a treatment plan, and/or to establish a virtual shared session, among other things.

The one or more machine learning models 13 may be trained to match patterns of a first set of parameters (e.g., user characteristics, treatment data, measures of benefits of exercises provided to users, probabilities of user compliance associated with the exercises, etc.) with a second set of parameters associated with an optimal treatment plan. The one or more machine learning models 13 may be trained to receive the first set of parameters as input, map the characteristics to the second set of parameters associated with the optimal treatment plan, and select the optimal treatment plan. The one or more machine learning models 13 may also be trained to control, based on the treatment plan, the treatment apparatus 70.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

Further, in some embodiments, based on subsequent data (e.g., user characteristics, treatment data, measures of exercise benefit data, probabilities of user compliance data, treatment plan result data, etc.) received, the machine learning models 13 may be continuously or continually updated. For example, the machine learning models 13 may include one or more hidden layers, weights, nodes, parameters, and the like. As the subsequent data is received, the machine learning models 13 may be updated such that the one or more hidden layers, weights, nodes, parameters, and the like are updated to match or be computable from patterns found in the subsequent data. Accordingly, the machine learning models 13 may be re-trained on the fly as subsequent data is received, and therefore, the machine learning models 13 may continue to learn.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

In some embodiments, the output device 54 may present a user interface that may present a recommended treatment plan, excluded treatment plan, or the like to the patient. The user interface may include one or more graphical elements that enable the user to select which treatment plan to perform. Responsive to receiving a selection of a graphical element (e.g., "Start" button) associated with a treatment plan via the input device 54, the patient interface 50 may communicate a control signal to the controller 72 of the treatment apparatus, wherein the control signal causes the treatment apparatus 70 to begin execution of the selected treatment plan. As described below, the control signal may control, based on the selected treatment plan, the treatment apparatus 70 by causing actuation of the actuator 78 (e.g., cause a motor to drive rotation of pedals of the treatment apparatus at a certain speed), causing measurements to be obtained via the sensor 76, or the like. The patient interface 50 may communicate, via a local communication interface 68, the control signal to the treatment apparatus 70.

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment apparatus 70 may be any suitable medical, rehabilitative, therapeutic, etc. apparatus configured to be controlled distally via another computing device to treat a patient and/or exercise the patient. The treatment apparatus 70 may be an electromechanical machine including one or more weights, an electromechanical bicycle, an electromechanical spinwheel, a smart-mirror, a treadmill, or the like. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force, a position, a speed, a velocity, and/or an acceleration. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for an assistant, such as a doctor, a nurse, a physical therapist, or a technician, to remotely communicate with the patient interface 50 and/or the treatment apparatus 70. Such remote communications may enable the assistant to provide assistance or guidance to a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58. The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a to the treatment apparatus 70 in response to an apparatus control signal 99a within the telemedicine signal 96, 97, 98a, 98b, 99a, 99b from the assistant interface 94. In some embodiments, the assistant interface 94 transmits the apparatus control signal 99a (e.g., control instruction that causes an operating parameter of the treatment apparatus 70 to change) to the treatment apparatus 70 via any suitable network disclosed herein.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the assistant may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the assistant to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the assistant. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the assistant. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate treatment plans and/or excluded treatment plans for patients and generate the display screens including those treatment plans and/or excluded treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as an assistant remotely from any conventional office infrastructure. Such remote work may be performed, for example, where the assistant interface 94 takes the form of a computer and/or telephone. This remote work functionality may allow for work-from-home arrangements that may include part time and/or flexible work hours for an assistant.

Figure 2:
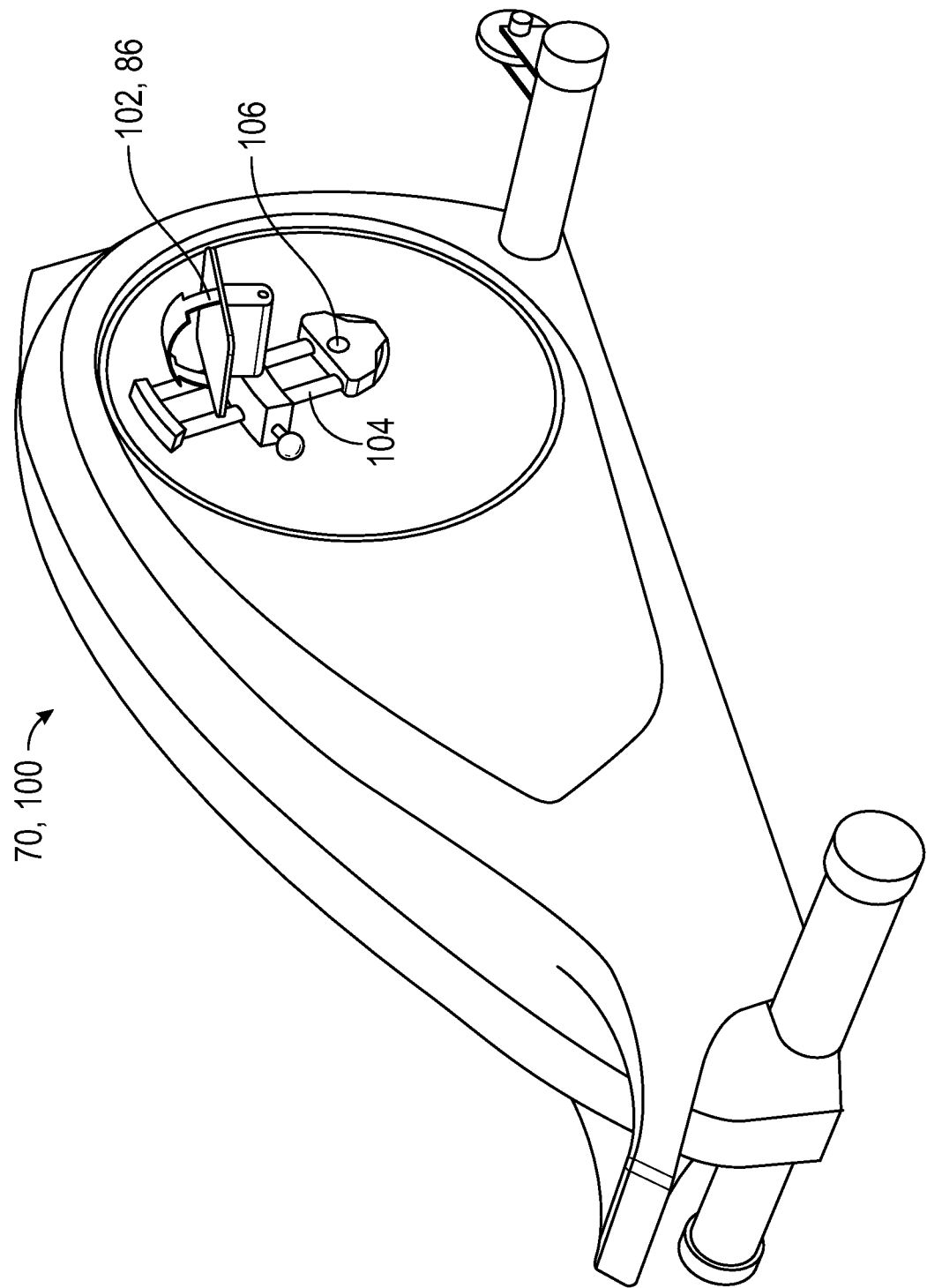
FIG. 2 shows a perspective view of an embodiment of a treatment apparatus according to the present disclosure.
Figure 3:
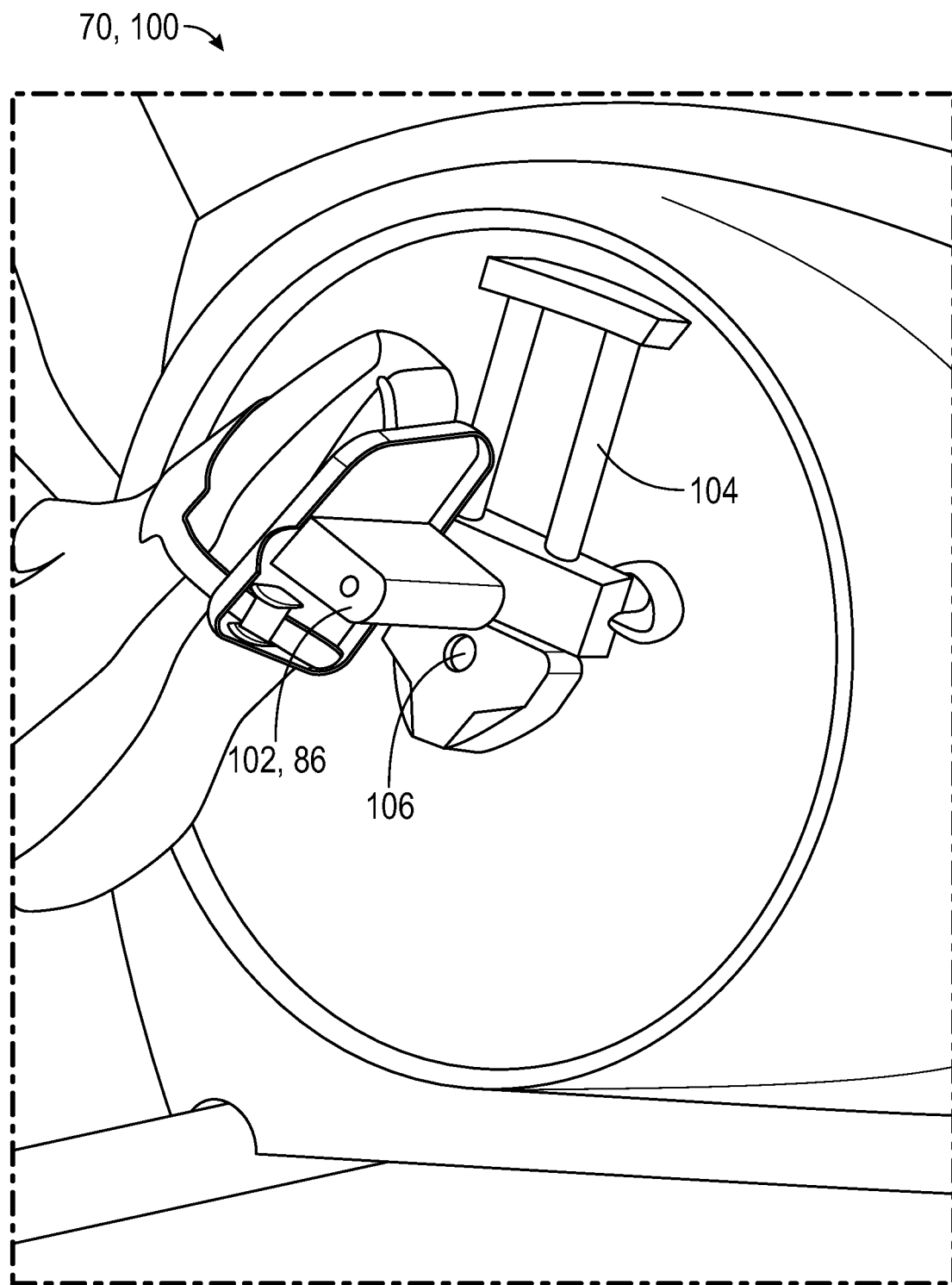
FIG. 3 shows a perspective view of a pedal of the treatment apparatus of FIG. 2 according to the present disclosure.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
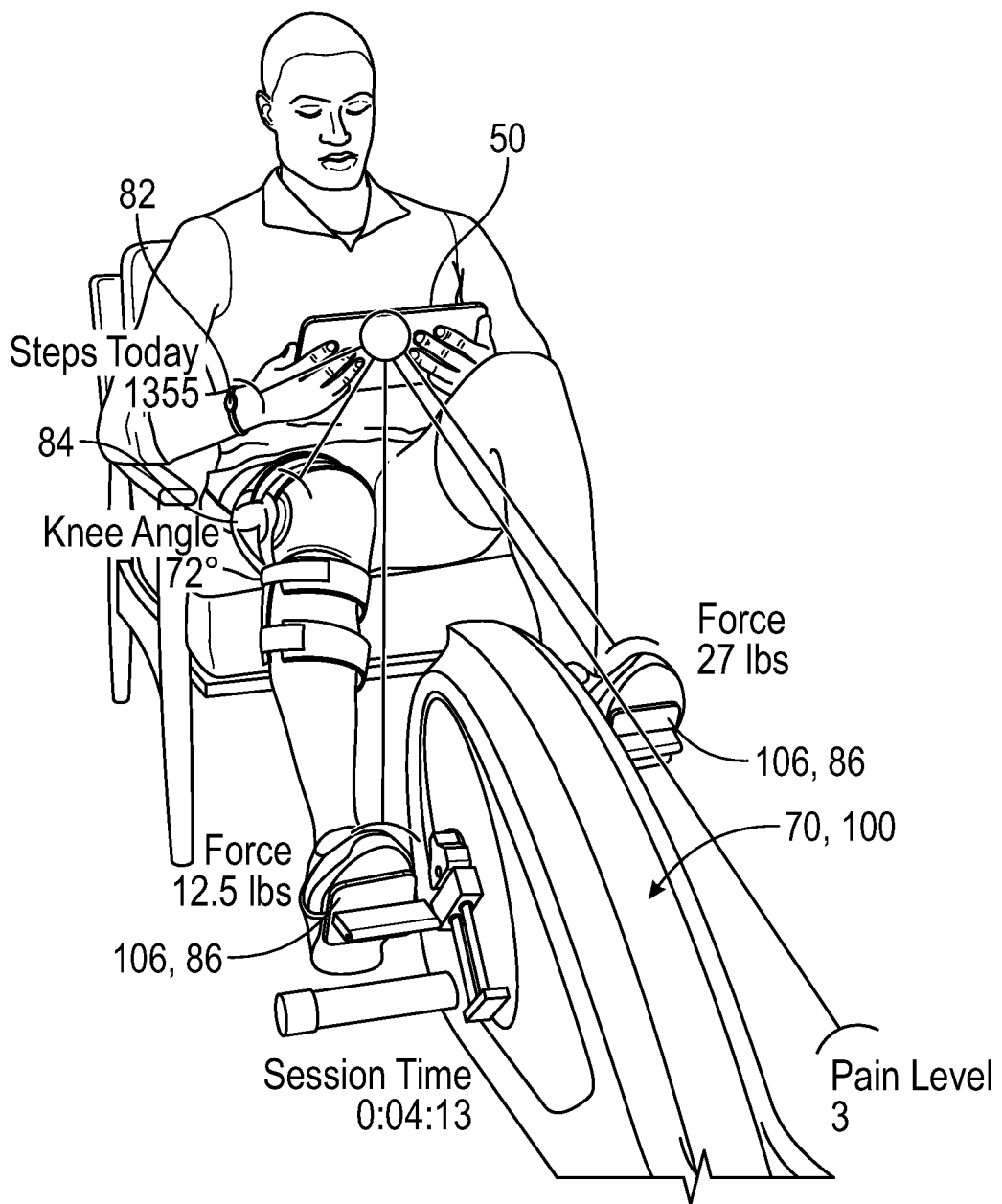
FIG. 4 shows a perspective view of a person using the treatment apparatus of FIG. 2 according to the present disclosure.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

Figure 5:
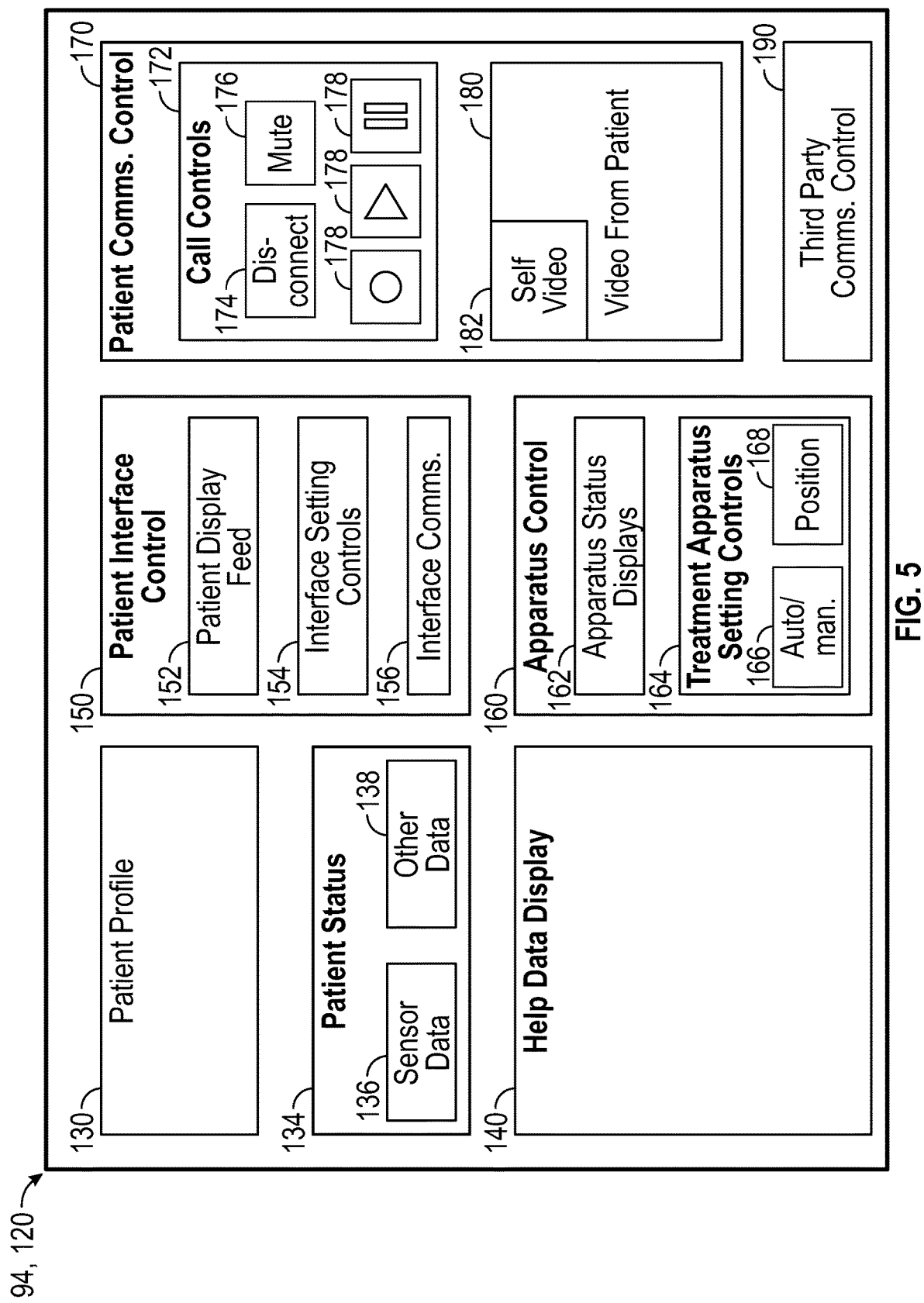
FIG. 5 shows an example embodiment of an overview display of an assistant interface according to the present disclosure.

FIG. 5 is an example embodiment of an overview display 120 of the assistant interface 94. Specifically, the overview display 120 presents several different controls and interfaces for the assistant to remotely assist a patient with using the patient interface 50 and/or the treatment apparatus 70. This remote assistance functionality may also be called telemedicine or telehealth.

Specifically, the overview display 120 includes a patient profile display 130 presenting biographical information regarding a patient using the treatment apparatus 70. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the assistant's need for that information. For example, a healthcare professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment apparatus 70. Such treatment plan information may be limited to an assistant who is a healthcare professional, such as a doctor or physical therapist. For example, a healthcare professional assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended treatment plans and/or excluded treatment plans may be presented in the patient profile display 130 to the assistant. The one or more recommended treatment plans and/or excluded treatment plans may be generated by the artificial intelligence engine 11 of the server 30 and received from the server 30 in real-time during, inter alia, a telemedicine or telehealth session.

The example overview display 120 shown in FIG. 5 also includes a patient status display 134 presenting status information regarding a patient using the treatment apparatus. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the assistant to use in determining a root cause and/or solution to a patient's problem. In some embodiments, the assistant interface 94 may present two or more help data displays 140, which may be the same or different, for simultaneous presentation of help data for use by the assistant. For example, a first help data display may be used to present a troubleshooting flowchart to determine the source of a patient's problem, and a second help data display may present script information for the assistant to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98b. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the assistant to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the assistant to remotely view and/or control the patient interface 50. For example, the patient interface setting control 154 may enable the assistant to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the assistant to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the assistant to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the assistant to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99b. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99a for changing an operating parameter of the treatment apparatus 70, (e.g., a pedal radius setting, a resistance setting, a target RPM, etc.). The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the assistant may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the assistant to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the assistant while the assistant uses the assistant interface 94. Alternatively or additionally, the audio and/or audiovisual communications may include communications with a third party. For example, the system 10 may enable the assistant to initiate a 3-way conversation regarding use of a particular piece of hardware or software, with the patient and a subject matter expert, such as a healthcare professional or a specialist. The example patient communications control 170 shown in FIG. 5 includes call controls 172 for the assistant to use in managing various aspects of the audio or audiovisual communications with the patient. The call controls 172 include a disconnect button 174 for the assistant to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session. The call controls 172 also include a multimedia feed display 180 for presenting still and/or video images from the patient interface 50, and a self-video display 182 showing the current image of the assistant using the assistant interface. The self-video display 182 may be presented as a picture-in-picture format, within a section of the multimedia feed display 180, as shown in FIG. 5. Alternatively or additionally, the self-video display 182 may be presented separately and/or independently from the multimedia feed display 180.

The example overview display 120 shown in FIG. 5 also includes a third party communications control 190 for use in conducting audio and/or audiovisual communications with a third party. The third party communications control 190 may take the form of a portion or region of the overview display 120, as shown in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a healthcare professional or a specialist. The third party communications control 190 may include conference calling capability for the third party to simultaneously communicate with both the assistant via the assistant interface 94, and with the patient via the patient interface 50. For example, the system 10 may provide for the assistant to initiate a 3-way conversation with the patient and the third party.

Figure 6:
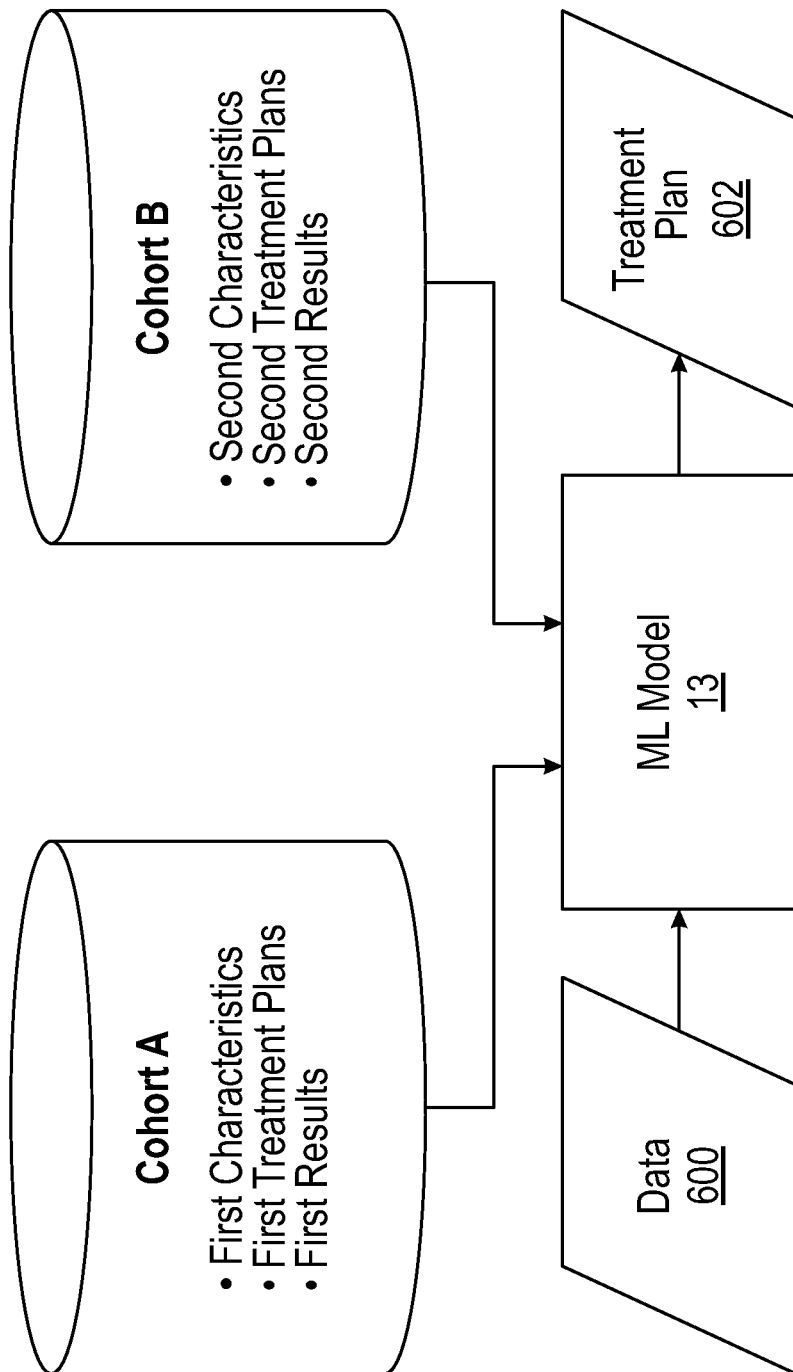
FIG. 6 shows an example block diagram of training a machine learning model to output, based on data pertaining to the patient, a treatment plan for the patient according to the present disclosure.

FIG. 6 shows an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the treatment apparatus 70 for 30 minutes 5 times a week for 3 weeks, wherein values for the properties, configurations, and/or settings of the treatment apparatus 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan 602. In some embodiments, the machine learning model 13 may be trained to output one or more excluded treatment plans that should not be performed by the new patient.

Figure 7:
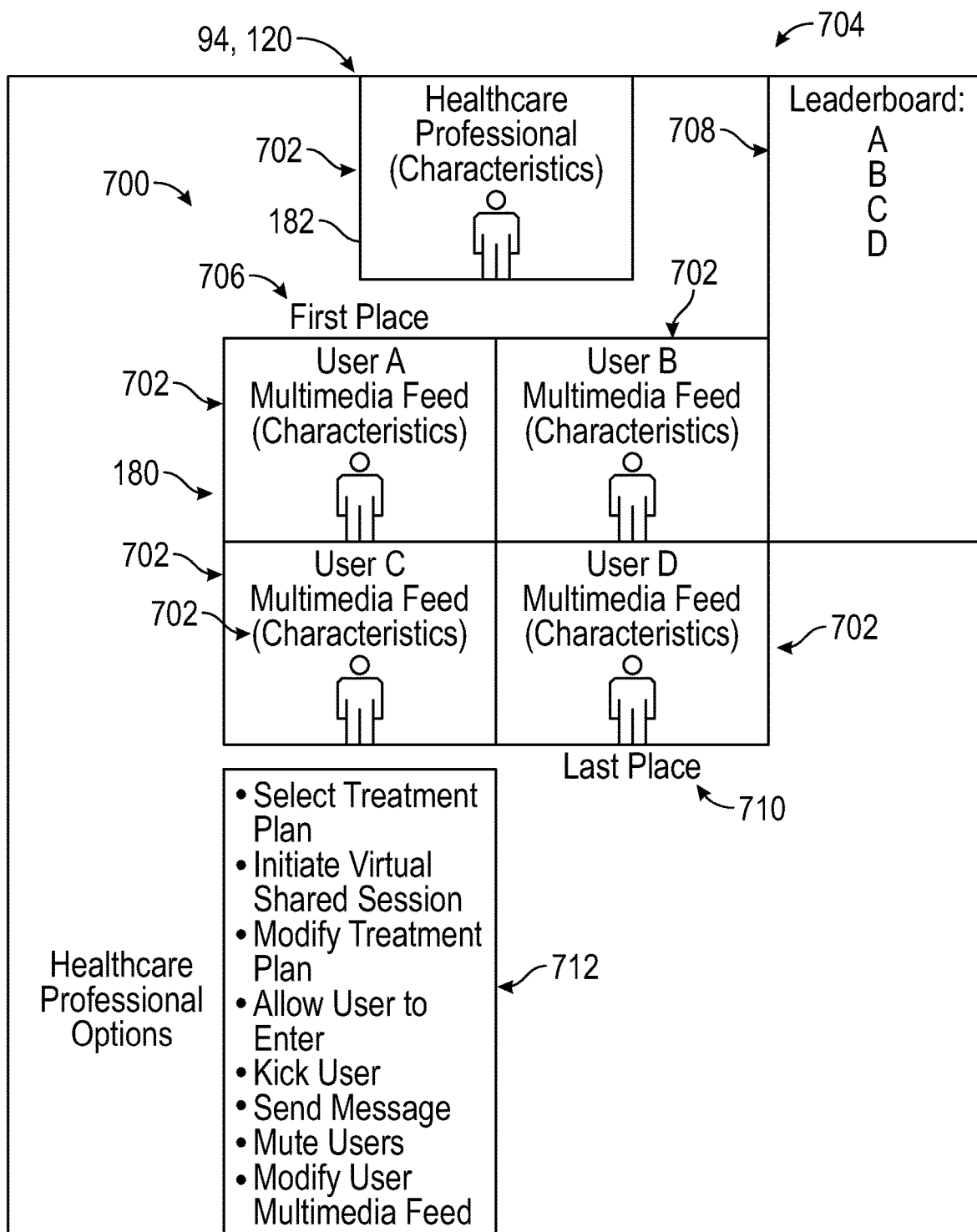
FIG. 7 shows an embodiment of an overview display of the assistant interface presenting a layout of multimedia feeds engaged in a virtual shared session according to the present disclosure.

FIG. 7 shows an embodiment of an overview display of the assistant interface 94 presenting a layout 700 of multimedia feeds 702 engaged in a virtual shared session 704 according to the present disclosure. A layout 700 may refer to an arrangement of multimedia feeds 702 and/or user characteristics in a particular graphical, linear, logical, process-based or other order in a user interface. The multimedia feeds 702 and/or user characteristics may be presented in different respective tiles, locations, and/or positions in any suitable, desirable, and/or configurable arrangement in a layout. Each different layout 704 may arrange at least one multimedia feed 702 and/or user characteristic in a different tile, location, or position from other layouts. As depicted, the overview display 120 includes the multimedia feed 702 of the healthcare professional in the self-video display 182, and the multimedia feeds 702 of the users in the multimedia feed display only include sections for the patient profile 130 and the multimedia feed display 180, including the self-video display 182.

The AI engine 11 may receive a set of characteristics pertaining to a set of users who desire to and/or are required to participate in a virtual shared session. The virtual shared session may be a telemedicine session, a rehabilitation session, a prehabilitation session, an exercise session, a support group session (e.g., cancer, substance abuse (e.g., illegal drugs, prescription drug abuse, alcohol, other addictive substances, etc.), autism, ambulatory, motor or motor neuron related, neurodegenerative, mental health, PTSD, etc.). The techniques described herein may determine, based on various information of the users (e.g., the characteristic data, vital sign data, user performance data, compliance data, therapy data, or the like), a first layout 700 to present on the computing devices of the users participating in the virtual shared session 704. In some embodiments, the characteristic data may include ratings valued according to one or more of user performance statistics (e.g., pedaling speed, range of motion, amount of force exerted on pedals, etc.), a prehabilitation and/or rehabilitation state (e.g., percentage of recovery, level of recovery, etc.), or the like.

The one or more machine learning models 13 may be trained to determine the first layout 700. The one or more machine learning models 13 may be trained based on the characteristics, vital sign data, user performance data, compliance data, and/or therapy data, or the like. As depicted, the first layout 700 includes a multimedia feed 702 for the healthcare professional, and four multimedia feeds 702 for four users A, B, C, and D. Also, characteristics pertaining to each user are presented in each multimedia feed 702. In some embodiments, presentation of the characteristics may include performance statistics of how the users are performing during the virtual shared session 704. It should be noted that, during the virtual shared session 704, as the users' characteristics change, the multimedia feeds 702 of the users A, B, C, and D may be dynamically rearranged in different layouts 700. The rearranging may be performed to encourage compliance with a treatment plan, such that a certain outcome is achieved (e.g., prehabilitation, rehabilitation, etc.).

To encourage compliance, the virtual shared session 704 may use the characteristics of the users to rank the users via a leaderboard 708 and layout locations of multimedia feeds 702 on the user interface. For example, there may be a location 706 on the user interface that is designated as being in first place. The location 706 may be defined using metadata and/or programmed to be present at certain pixels. There may be a location 710 on the user interface that is designated as being in last place. The location 706 may be defined using metadata and/or programmed to be present at certain pixels. The leaderboard 708 presents an identity (e.g., name, identifier, alphanumeric symbol, a graphic image, etc.) pertaining to each user A, B, C, and D. Currently, as depicted in leaderboard 708's example, user A is in first place, and thus, the multimedia feed 702 for user A is arranged at the location 706 designated as first place, and the leaderboard 708 reflects that user A is in first place because A is at the top of the list. Further, user B is in second place on the leaderboard 708 and user B's multimedia feed 702 is at a location designated as second place in the layout 700.

When the virtual shared session 704 is initiated, the first layout 700 may be presented in real-time and/or near real-time on each computing device of the users participating in the virtual shared session 704. In some embodiments, the first layout 700 may be presented as projections on various surfaces (e.g., wall, floor, ceiling, etc.), inside one or more virtual reality and/or augmented reality headsets, or some combination thereof. The projections may arise out of one or more virtual reality and/or augmented reality devices.

In some embodiments, each of the users may be using respective treatment apparatuses 70 to perform a treatment plan and/or exercise. During the virtual shared session 704, characteristic data (e.g., statistics (pedaling speed, range of motion, force exerted on pedals), heartrate, blood pressure, vital signs, measurements of pain, etc.) may be received from the treatment apparatuses 70 and/or any suitable source (e.g., sensors, computing device of the user, etc.). The AI engine 11 (via machine learning models 13) may determine that the characteristics for one user necessitate generating a new layout 700 by rearranging the multimedia feeds 702, the user characteristics, and/or the identities on the leaderboard 708. For example, if user B begins pedaling faster than user A, the machine learning models 13 may determine to rearrange the multimedia feed, such that user B is at the location 706 designated as first place and that the multimedia feed for user A is moved to the location designated as second place. Also, the identity of user B may be switched with the identity of user A on the leaderboard 708. Such techniques may provide a technical solution that encourages competition, which may result in enhanced compliance with treatment plans. The enhanced compliance may result in improved prehabilitation and/or rehabilitation.

In some embodiments, during the virtual shared session 704, the characteristics (e.g., performance statistics, ratings, etc.) of all the users may be presented in the layout 700 on all of the computing devices associated with all the users. In certain instances, a user may desire not to allow other users to view their characteristics, and the user may opt out of allowing others to view the user's characteristics.

In some embodiments, a rating system may be used to determine whether or not to arrange multimedia feeds 702. For example, a user may be provided a low rating if they just began rehabilitation after surgery (e.g., have a low range of motion), and a user may be provided a high rating if they are further along in their rehabilitation (e.g., have a high range of motion). During the virtual shared session 704, the rating system may be used to level the playing field, such that the user with the low rating is not penalized (e.g., multimedia feed 702 being moved to a worse location (e.g., location 708) in the layout 700, but their identity is not moved lower on the leaderboard 708) for being unable to achieve a high range of motion attained by the higher rated user.

The overview display 120 also includes various healthcare professional options, such as options for selecting a treatment plan to be performed during the virtual shared session 704, initiating the virtual shared session 704, modifying the treatment plan, allowing a user to enter the virtual shared session 704, ejecting a user from the virtual shared session 704 (e.g., for breaking a rule, using profanity, etc.), sending a message or notification to a computing device of a user participating in the virtual shared session 704, muting one or more users, and/or modifying a user's multimedia feed 702 (e.g., blacking it out, implementing a blurring effect, implementing an augmented reality object, etc.). The healthcare professional options may be implemented as graphical elements (e.g., buttons, drop-down list, etc.) selectable via an input peripheral (e.g., mouse, keyboard, touchscreen, microphone, etc.). Selection of a healthcare professional option may cause its respective operation to be performed.

Figure 8:
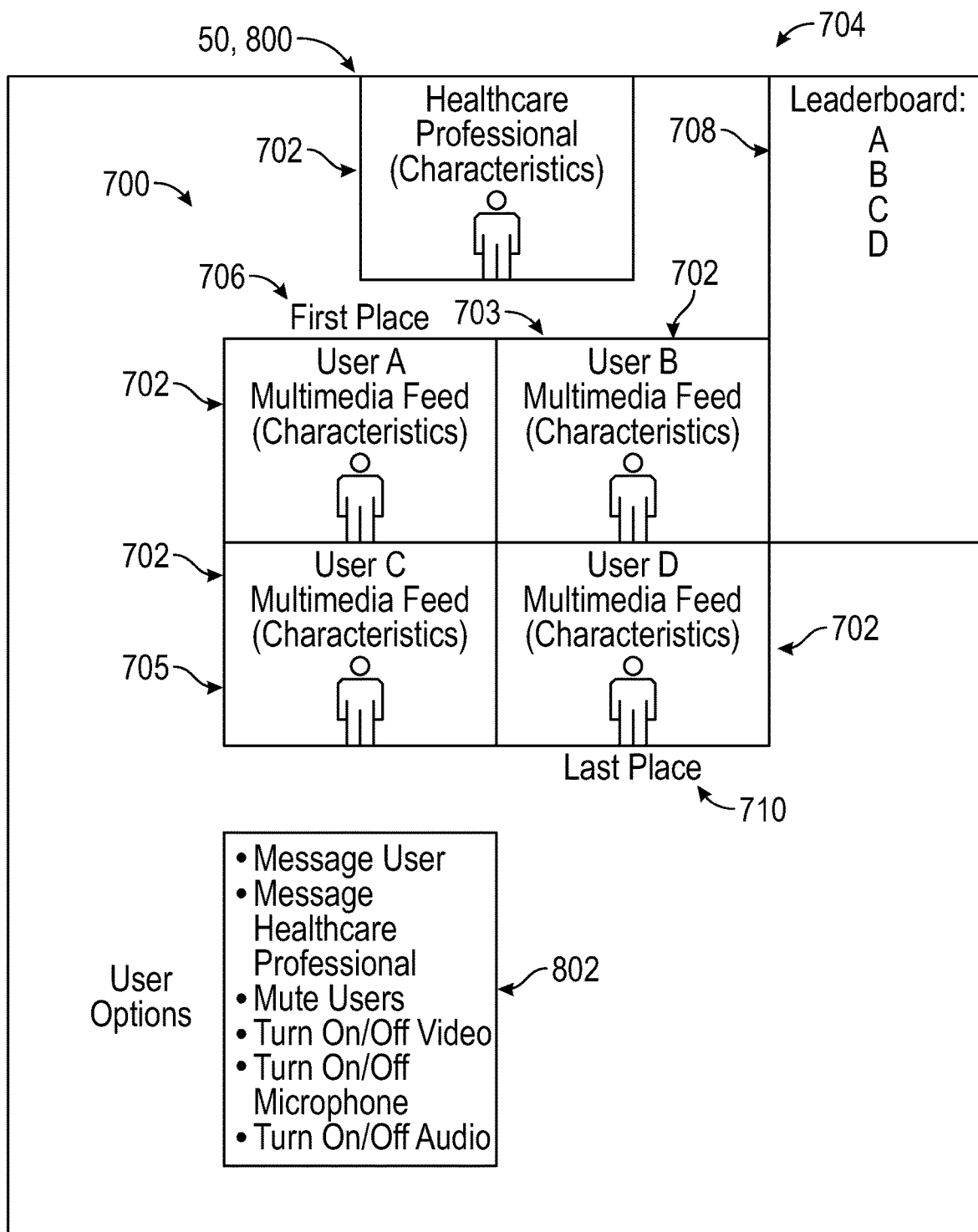
FIG. 8 shows an embodiment of an overview display of a patient interface presenting a first layout of multimedia feeds arranged in a first order according to the present disclosure.

FIG. 8 shows an embodiment of an overview display 800 of a patient interface 50 presenting a first layout 700 of multimedia feeds 702 arranged in a first order according to the present disclosure. The layout 700 in FIG. 8 presents the multimedia feeds 702 of users A, B, C, and D, the same as depicted in FIG. 7. For example, user A's multimedia feed 702 is arranged at the location 706 designated as first place, user B's multimedia feed 702 is arranged at the location 703 designated as second place, user C's multimedia feed 702 is arranged at the location 705 designated as third place, and user D's multimedia feed is arranged at the location 710 designated as fourth place. Each user's characteristics (e.g., statistics, ratings, etc.) may be presented relative to each user's multimedia feed 702. In some embodiments, only the healthcare professional may view the characteristics of the users. Further, the leaderboard 708 indicates that A is in first place, B is in second place, C is in third place, and D is in fourth place.

The overview display 800 includes user options, such as options for messaging a user participating in the virtual shared session 704, messaging the healthcare professional privately, muting one or more users participating in the virtual shared session 704, turning on/off video output from a multimedia feed 702 of one or more users, turning on/off a microphone, and/or turning on/off audio from a multimedia feed 702 associated with one or more users. The user options may be implemented as graphical elements (e.g., buttons, drop-down list, etc.) selectable via an input peripheral (e.g., mouse, keyboard, touchscreen, microphone, etc.). Selection of a user option may cause its respective operation to be performed.

The server 30 (e.g., AI engine 11) may initiate the virtual shared session 704. During the virtual shared session 704, as users use their respective treatment apparatuses 70, subsequent characteristics pertaining to the users may be received by the machine learning models 13. The machine learning models 13 may determine, based on the subsequent characteristics, to generate a new layout by rearranging the multimedia feeds 702, or rearranging characteristics of the users (e.g., the identities of the users on the leaderboard 708), or both. In some embodiments, the machine learning models 13 may rearrange both the locations of the multimedia feeds 702 and the identities of the users on the leaderboard 708. In some embodiments, the machine learning models 13 may rearrange only the identities of the users on the leaderboard 708, while maintaining the arrangement of the multimedia feeds 702.

Figure 9:
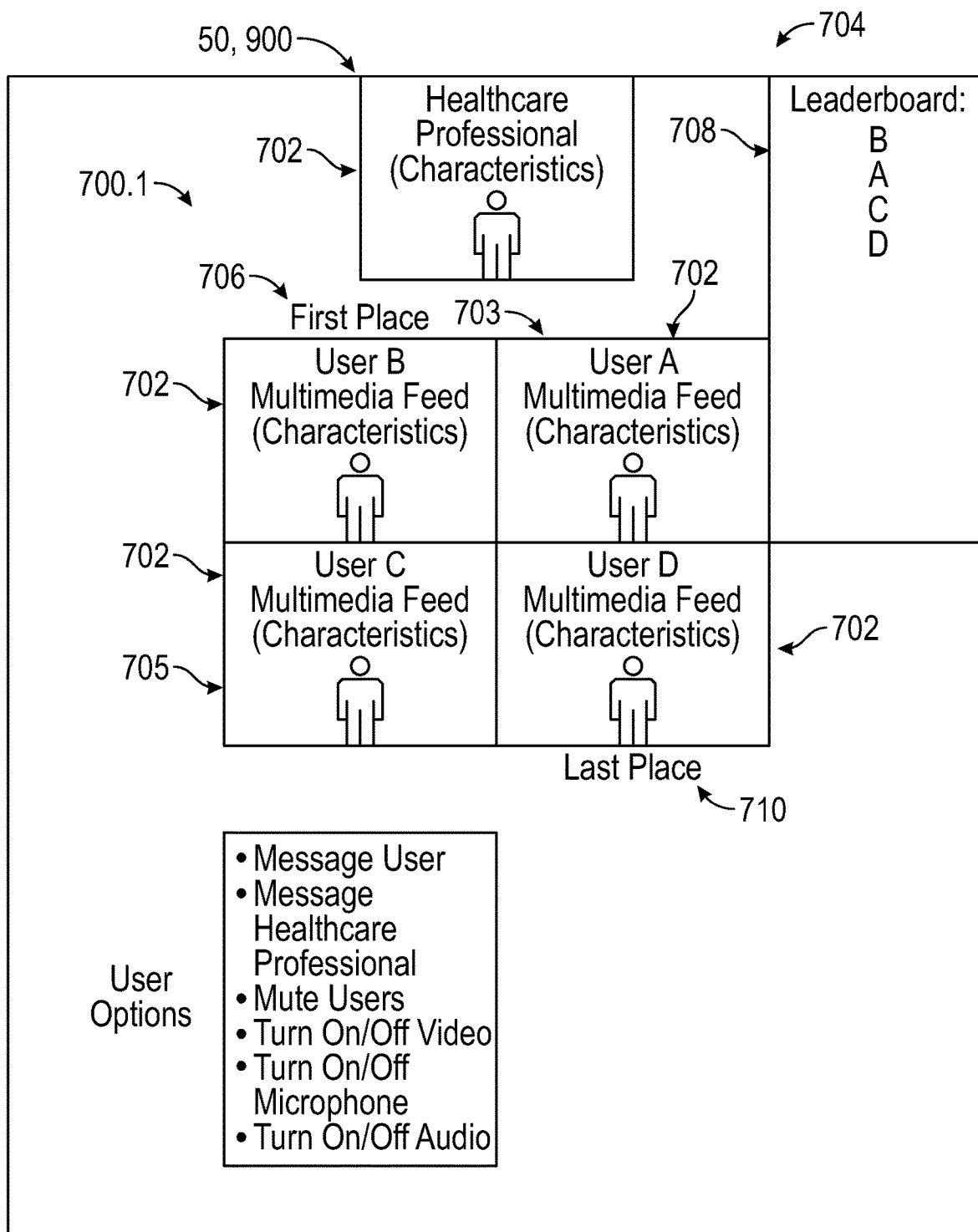
FIG. 9 shows an embodiment of an overview display of a patient interface presenting a layout of multimedia feeds arranged in a second order according to the present disclosure.

To illustrate a rearrangement scenario, FIG. 9 shows an embodiment of an overview display 800 of a patient interface 50 presenting a layout 700.1 of multimedia feeds 702 arranged in a second order according to the present disclosure. During the virtual shared session 704, the machine learning models 13 may receive subsequent characteristics pertaining to the users and generate, based on the subsequent characteristics, the layout 700.1. The subsequent characteristics may include information that indicates user B is pedaling faster on the treatment apparatus 70 than user A. Accordingly, the machine learning models 13 may rearrange the multimedia feed 702 for user B to be at the location 706 designated for first place and the multimedia feed 702 for user A to be at the location 703 for second place. Also, as depicted, the machine learning models 13 rearranged the identity of user B to be at first place on the leaderboard 708 and the identity of user A to be at second place on the leaderboard.

Figure 10:
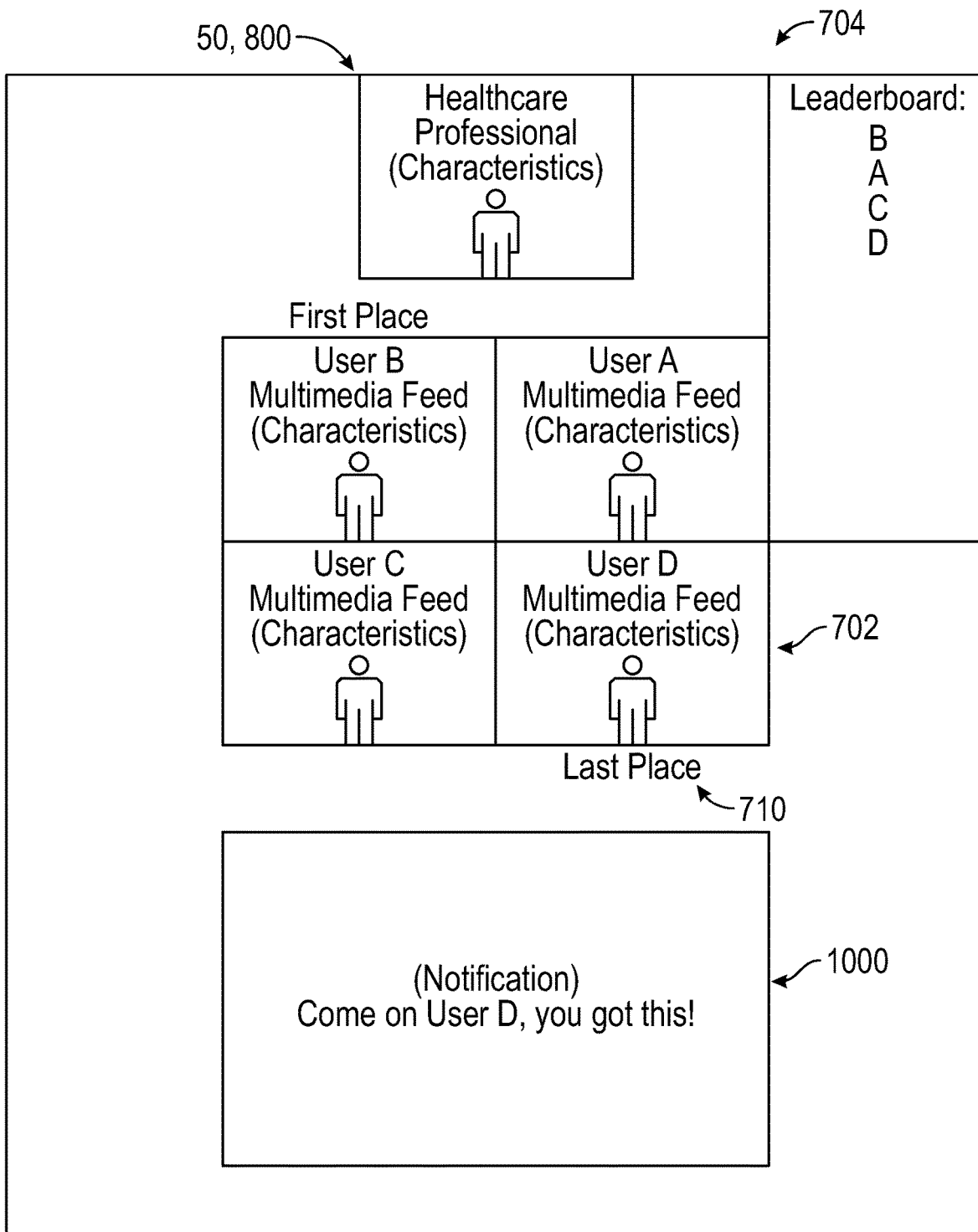
FIG. 10 shows an embodiment of an overview display of a patient interface presenting a notification during a virtual shared session according to the present disclosure.

FIG. 10 shows an embodiment of an overview display 800 of a patient interface 50 presenting a notification 1000 during a virtual shared session 704 according to the present disclosure. The one or more machine learning models 13 may be trained to determine, based on received characteristics of users and/or placement information (e.g., first, second, third, fourth (last)), to transmit the notification 1000 to a computing device of a user at a certain time. For example, as depicted, user D's multimedia feed 702 is arranged at the location 710 designated as being in last place. The machine learning models 13 may be trained to send the notification 1000 within a threshold period of time (e.g., milliseconds, 1 second, 5 seconds, a minute, etc.) of a multimedia feed 702 being arranged at the last place location 710. Accordingly, the patient interface 50 (computing device) depicted is associated with user D, and the machine learning models 13 cause the notification 710 to be transmitted for presentation on user D's computing device. The notification 1000 may include a motivational message (e.g., "COME ON USER D, YOU GOT THIS!").

In some embodiments, the notification 1000 may include an incentive offer, such as a reward that may be deposited in a digital wallet of the user if the user accomplishes a particular goal (e.g., achieving first place, satisfying a threshold performance (pedaling speed)). Such techniques may further enhance compliance with a treatment plan.

Figure 11:
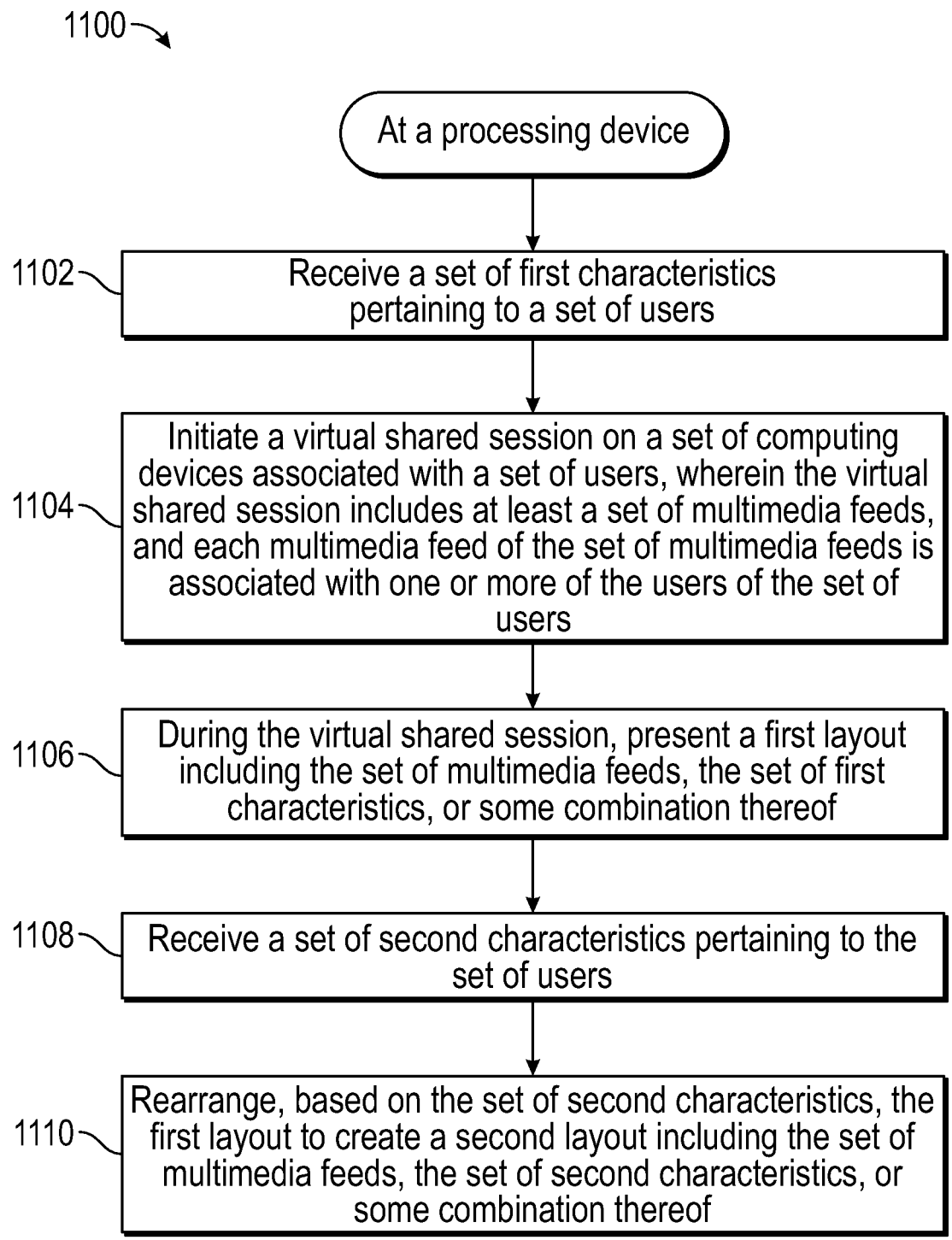
FIG. 11 shows an example embodiment of a method for changing layouts of multimedia feeds based on characteristics of users in a virtual shared session according to the present disclosure.

FIG. 11 shows an example embodiment of a method 1100 for changing layouts of multimedia feeds based on characteristics of users in a virtual shared session according to the present disclosure. The method 1100 is performed by processing logic that may include hardware (circuitry, dedicated logic, etc.), software (such as is run on a general-purpose computer system or a dedicated machine), communicative coupling, or a combination of both. The method 1100 and/or each of its individual functions, routines, other methods, scripts, subroutines, or operations may be performed by one or more processors of a computing device (e.g., any component of FIG. 1, such as server 30 executing the artificial intelligence engine 11). In certain implementations, the method 1100 may be performed by a single processing thread. Alternatively, the method 1100 may be performed by two or more processing threads, each thread implementing one or more individual functions, methods (in the computer science/object-oriented definition) or routines; or other methods (in the computer science/object-oriented definition), scripts, subroutines, or operations of the methods (in the computer science/object-oriented definition).

For simplicity of explanation, the method 1100 is depicted and described as a series of operations. However, operations in accordance with this disclosure can occur in various orders and/or concurrently, and/or with other operations not presented and described herein. For example, the operations depicted in the method 1100 may occur in combination with any other operation of any other method disclosed herein. Furthermore, not all illustrated operations may be required to implement the method 1100 in accordance with the disclosed subject matter. In addition, those skilled in the art will understand and appreciate that the method 1100 could alternatively be represented as a series of interrelated states via, e.g., a state diagram, a directed graph, a deterministic finite state automaton, a non-deterministic finite state automaton, a Markov diagram, or an event diagram.

At 1102, the processing device may receive a set of characteristics pertaining to a set of users. The set of users may include a healthcare professional, a patient, a participant, a volunteer, or some combination thereof. The set of characteristics may be any suitable characteristic as described herein. In some embodiments, the set of characteristics may include one or more statistics pertaining to the user, such as range of motion (e.g., degree of extension and/or flexion), pedaling speed (e.g., average speed, fastest speed, slowest speed, etc.), force exerted on pedals (e.g., average force, largest force, smallest force, etc.), state of rehabilitation of a body part (e.g., a state of recovery, a pain level, etc.), a rating (the rating may be determined by the state of rehabilitation, the state of rehabilitation as compared to other users in a particular cohort, etc.), and the like.

At 1104, the processing device may initiate a virtual shared session 704 on a set of computing devices associated with a set of users. The virtual shared session 704 may include at least a set of multimedia feeds 702, and each multimedia feed 702 of the set of multimedia feeds 702 is associated with one or more of the users of the set of users. In some embodiments, there may be a one-to-one relationship between the multimedia feed 702 and one or more sets of users, a one-to-many relationship between the multimedia feed 702 and one or more sets of users, a many-to-one relationship between the multimedia feed 702 and one or more sets of users, or a many-to-many relationship between the multimedia feed 702 and one or more sets of users.

The virtual shared session 704 may pertain to rehabilitative therapy, prehabilitative therapy, strength training, mental health therapy, an exercise session, or some combination thereof. In some embodiments, each user of the set of users is using a respective treatment apparatus 70 to perform a treatment plan, exercise, therapeutic activity, etc. In some embodiments, the virtual shared session 704 may include a telemedicine session wherein at least one of the set of computing devices is an assistant interface 50 associated with a healthcare professional.

A multimedia feed 702 may refer to live (e.g., real-time or near real-time) or prerecorded media (e.g., audio content, video content, and/or audiovisual content). A stream of bits representing the multimedia feed 702 may be transmitted from each computing device to the server 30 and/or the other computing devices involved in the virtual shared session 704. The server 30 may directly or indirectly relay the stream of bits to each of the other computing devices involved in the virtual shared session 704. The stream of bits may include audio data, video data, audiovisual data, vibrational data, force data, acceleration data, or some combination thereof. The acceleration data may be used to create an enhanced experience. The stream of bits may be delivered through the treatment apparatus to provide feedback. The pedals may vibrate to indicate attaining a certain threshold of speed and/or force. The resistance of the rotation may increase (force data) to simulate climbing an inclined object (e.g., hill) and then decrease to indicate reaching the top of the inclined object (e.g., top of the hill). Reaching the top of the inclined object may be accommodated by receiving a digital reward (e.g., a deposit in a digital wallet, an advertisement, a coupon, an email, a text, etc.). Based on the stream of bits, the treatment apparatus 70 may change a set speed or acceleration rate to indicate reaching a certain threshold. In some embodiments, if the users configure how they desire their multimedia feed 702 to be presented in the virtual shared session 704, the server 30 may process the stream of bits based on the configuration (e.g., using augmented reality, blurring effects on the video, voice modulation for the audio, etc.). The stream of bits may be received by a processing device and processed to output the multimedia feed 702.

At 1106, during the virtual shared session 704, the processing device may present a first layout 700 including the set of multimedia feeds 702, the set of first characteristics, or some combination thereof. In some embodiments, the first layout may be presented on a set of displays of the set of computing devices communicatively coupled in the virtual shared session 704, as a set of projections on a set of surfaces, inside one or more virtual reality or augmented reality headsets, or some combination thereof. In some embodiments, the projection may arise (e.g., be rendered, generated, transmitted, etc.) out of one or more virtual reality or augmented reality devices.

In some embodiments, different subsets of the set of first characteristics are associated with different respective users of the set of users. Each subset may be presented relative to the multimedia feed 702 associated with its respective associated user. For example, each subset of characteristics for each user may be presented in a respective portion of a user interface. The respective portion of the user interface may also present each multimedia feed 702 associated with each user.

At 1108, the processing device may receive a set of second characteristics pertaining to the set of users. In some embodiments, either or both of the plurality of first characteristics and the plurality of second characteristics are received from a plurality of sources comprising a treatment apparatus 70, a sensor, a camera, a computing device, biometric sensors, software, a database, or some combination thereof.

At 1110, the processing device may rearrange, based on the set of second characteristics, the first layout 700 to create a second layout 700.1 including the set of multimedia feeds 702, the set of second characteristics, or some combination thereof. In some embodiments, the first layout 700 and the second layout 700.1 are determined by one or more machine learning models 13 trained to determine layouts. The one or more machine learning models 13 may be trained using user characteristic data, vital sign data, user performance data, biometric data, compliance data, demographic data, therapy data, ratings data, geographic data, historical performance data, or some combination thereof. The first layout 700 and second layout 700 may include at least one of the multimedia feeds 702 or the characteristics arranged in a different order.

For example, in some embodiments, if the set of second characteristics indicates that a statistic related to pedaling speed increased for a user such that the user is now pedaling the fastest among the set of users, the second layout 700 may include the set of multimedia feeds rearranged such that the multimedia feed 702 associated with the user is itself arranged in a location 706 designated on the user interface as indicating the user to be in first place.

In some embodiments, dynamically rearranging the multimedia feeds 702, the characteristics associated with the users, or both, to generate and present layouts 700 may encourage users to comply with a treatment plan, thereby improving rehabilitation, prehabilitation, strength, fitness, mental health, etc. For example, such techniques may stimulate competition among the users by encouraging them to achieve first place during the virtual shared session 704. Achieving first place may refer to moving their multimedia feed 702 to a location 706 on the user interface then-designated as being in first place. The location may be defined using metadata and/or programmed to be present at certain pixels. When characteristics indicate the multimedia feeds are to be moved, a transformation may occur where the data representing the multimedia feeds 702 to be moved are remapped to appropriate locations on the user interface, thereby generating a new layout 700.

In some embodiments, the processing device may arrange the multimedia feeds 702 in a cooperative layout where the multimedia feeds 702 are similarly situated if the users associated with the multimedia feeds 702 are performing similarly (e.g., achieving a similar outcome). For example, some rehabilitative treatments (e.g., substance abuse, mental health, etc.) may be optimized when a cooperative layout is the targeted treatment goal for a cohort.

In some embodiments, the processing device may control, based on either or both of the set of first characteristics and the set of second characteristics, at least one treatment apparatus 70 used by at least one user of the set of users. In some embodiments, the processing device may actively control the treatment apparatus 70 during the virtual shared session 704. For example, the processing device may actively control the treatment apparatus 70 by transmitting a signal, including a control instruction, to the treatment apparatus 70, and the signal may be received by a processing device of the treatment apparatus 70, which is configured to execute the control instruction to change an operating parameter of the treatment apparatus 70.

In some embodiments, based on at least a portion of the set of first characteristics, the processing device may use one or more machine learning models 13 to provide a notification 1000 to a computing device of the set of computing devices. The notification 1000 may include text, audio, video, haptic feedback, or some combination thereof. In some embodiments, the notification 1000 may be a motivational message that is selected and sent by one or more machine learning models 13. The one or more machine learning models 13 may be trained to determine, based on characteristics of a user, that the user is struggling to perform a treatment plan or is not performing as well as the other users in the virtual shared session 704. Accordingly, the one or more machine learning models 13 may select, based on the characteristics of the user, an appropriate motivational message and transmit it to the computing device associated with the user.

In some embodiments, the processing device may determine a set of ratings for the set of users. The set of ratings may be based on electronic medical records (e.g., medical conditions, surgeries, medications, a glucose level, etc.), measurement data (e.g., sensor data for force, range of motion, etc.), the set of first characteristics, the set of second characteristics, or some combination thereof. During the virtual shared session 704, the processing device may receive a set of third characteristics pertaining to the set of users. The processing device may maintain, based on the set of ratings and the set of third characteristics, the second layout 700.1. Such a technique may enable leveling the playing field between the users participating in the virtual shared session. Essentially, the rating may be used to indicate that a person having a lower rating wherein the person is pedaling at a slow rate should not be penalized because a person having a higher rating is pedaling at a faster rate. The rating may be associated with the stage or state of rehabilitation of the users, among other things.

In some embodiments, the processing device may communicate the set of ratings and the set of third characteristics to one or more users. The communication may be private such that only the rated user is made aware of that user's own rating. Further, in some embodiments, a healthcare professional associated with the rated user may also be made aware of the user's rating. Sharing the user's rating with their healthcare professional may enable the healthcare professional to track the user's physiological, biochemical, psychological, and/or behavioral progress. The healthcare professional may choose, using a user interface, to modify, during the virtual shared session 704, based on the user's rating, the user's treatment plan, and the healthcare professional may select to control the treatment apparatus dynamically with the modified treatment plan. In some embodiments, the user's rating may be stored in a database and may be transmitted or otherwise provided to other healthcare professionals as desired (if the user registers with a new healthcare professional).

Figure 12A:
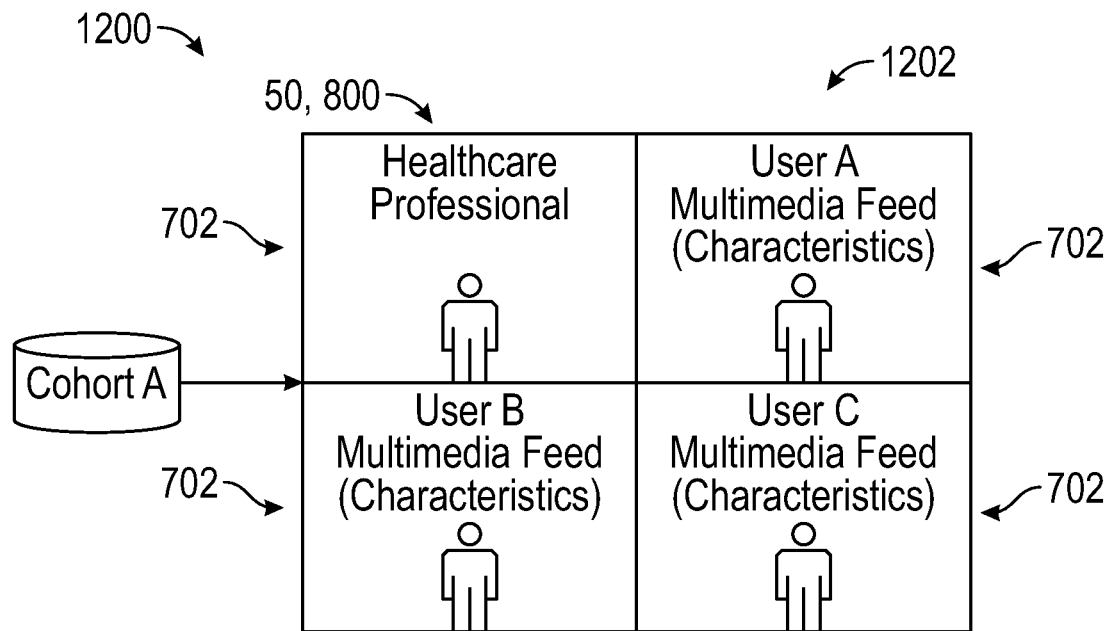
FIGS. 12A-B show embodiments for enabling virtual shared sessions for users that classify for certain cohorts according to the present disclosure.
Figure 12B:
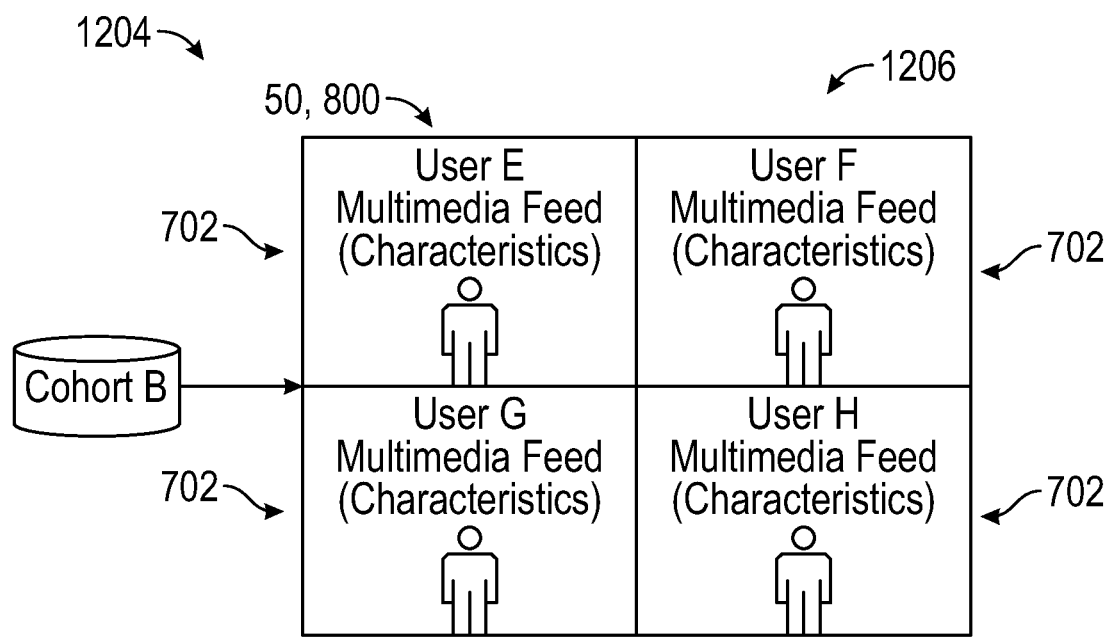

FIGS. 12A-B show embodiments of enabling virtual shared sessions 704 for users who classify to belong to certain cohorts according to the present disclosure. Each of the cohorts A and B may represent and be similar to the cohorts A and B depicted and described with reference to FIG. 6. In some embodiments, the cohorts A and B may also include users grouped based on characteristics pertaining to various ratings, such as a performance rating, a fitness rating, a rehabilitation rating, a prehabilitation rating, an exercise rating, an athleticism rating, a competition level rating, a credit rating, a personality assessment, a personality inventory, or some combination thereof. The cohorts A and B may also include users grouped based on characteristics pertaining to abilities, demographic data, psychographic data, medical conditions, personal or other attributes, and/or any suitable characteristics. In some embodiments, based on one or more characteristics, a user may be matched to one or more cohorts.

The cohorts may be used to establish "leagues" or "social networks" of users for participating in virtual shared sessions 704 with other users similarly situated. For example a user having a low performance rating (e.g., "100") may not match with a cohort including a user having a high performance rating (e.g., "1000"). As such, the user having the low rating may not be included in virtual shared session 704 in which the user having the high rating participates. Such a technique may prevent the user with the low rating from being embarrassed and may create "leagues" or "social networks" that are balanced in terms of characteristics. Further, it may enable a healthcare professional that guides the virtual shared session 704 to similarly modify treatment plans and/or operating parameters (e.g., increase the amount of resistance equally) of the treatment apparatuses 70 being used by the users. For the purposes of this disclosure, an artificial intelligence engine which performs many or all of the functions of such a healthcare professional shall also be deemed a healthcare professional.

To illustrate an example, FIG. 12A depicts a virtual shared session 1202 including users A, B, and C that matched with characteristics of users in cohort A. The virtual shared session 1202 is presented on the overview display 800 of the patient interface 50. Users in cohort A require a healthcare professional to be present during the virtual shared session 1202. For example, the users in cohort A may have a certain rating that indicates their rehabilitation is at a state where advancement cannot occur without the supervision of a healthcare professional. Users A, B, and C may be assigned such a rating. Accordingly, a virtual shared session 1202 is established between the computing devices of the users A, B, and C. The machine learning models 13 may be trained to match users requesting to start a virtual shared session 1202 with a cohort associated with certain user characteristics, and may generate a layout 1200 of multimedia feeds 702 associated with the users. The layout 1200 may be generated based on characteristics of the users, or the layout 1200 may be randomly generated.

As depicted, the layout 1200 includes a multimedia feed 702 of a healthcare professional, and multimedia feeds for users A, B, and C. Also, the characteristics of the users are presented relative to the users. In some embodiments, the healthcare professional may be the only user enabled to view the characteristics of the users. During the virtual shared session 1202, the layout 1200 may be implemented on the computing devices of the users.

In some embodiments, during the virtual shared session 1202, the patients may be using a treatment apparatus 70 to perform a treatment plan. The machine learning models 13 may control operation of the treatment apparatuses 70 according to the treatment plan by transmitting signals to the treatment apparatuses 70 that cause an operating parameter of the treatment apparatuses 70 to change. Further, the virtual shared session 1202 may be a telemedicine session and the healthcare professional may control, based on characteristics of the users and/or the treatment plan, the operation of the treatment apparatuses 70.

FIG. 12B depicts a virtual shared session 1206 including users E, F, G, and H that matched with characteristics of users in cohort B. The virtual shared session 1206 is presented on the overview display 800 of the patient interface 50. Users in cohort B may not require a healthcare professional to be present during the virtual shared session 1206. These virtual shared sessions may be user-led. For example, such a scenario may include a group of users who desire to virtually exercise together. The user characteristics associated with cohort B may indicate high performance ratings, such as professional athletes. Users E, F, G, and H having such high performance ratings may desire to train with each other in a virtual shared session 1206. Accordingly, the virtual shared session 1206 is established between the computing devices of the users A, B, and C. The machine learning models 13 may be trained to match users requesting to start a virtual shared session 1206 with a cohort associated with certain user characteristics, and may generate a layout 1204 of multimedia feeds 702 associated with the users. The layout 1204 may be generated based on characteristics of the users, or the layout 1204 may be randomly generated.

As depicted, the layout 1204 includes multimedia feeds for users E, F, G, and H. Also, the characteristics of the users are presented relative to the users. During the virtual shared session 1206, the layout 1204 may be implemented on the computing devices of the users.

In some embodiments, treatment plans for users assigned to cohort B may be implemented to control treatment apparatuses 70 during virtual shared session 1206. For example, during the virtual shared session 1206, to modify operating parameters of the treatment apparatuses 70, the machine learning models 13 may transmit signals with control instructions to the treatment apparatuses 70 associated with users in the virtual shared session 1206.

Figure 13A:
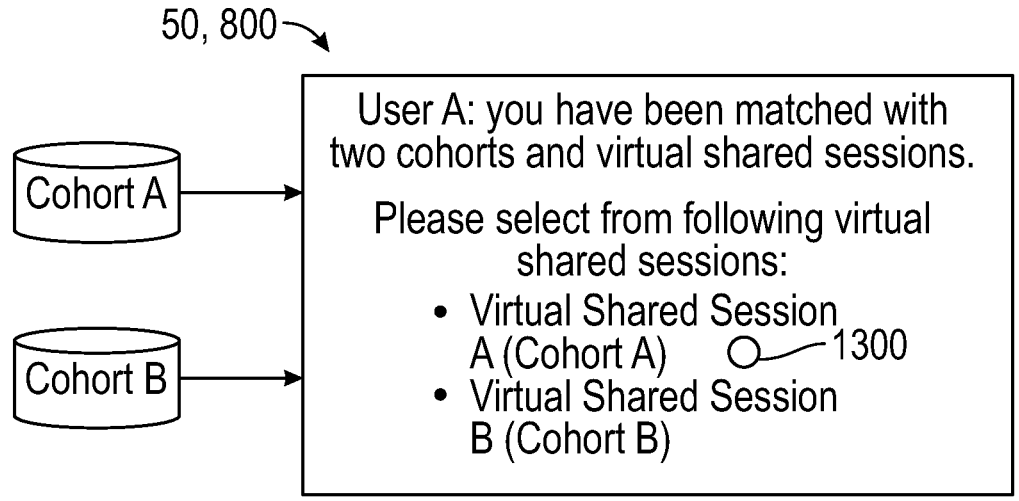
FIGS. 13A-B show an embodiment of a user classifying for two cohorts and enabling the user to select a virtual shared session to join according to the present disclosure.
Figure 13B:
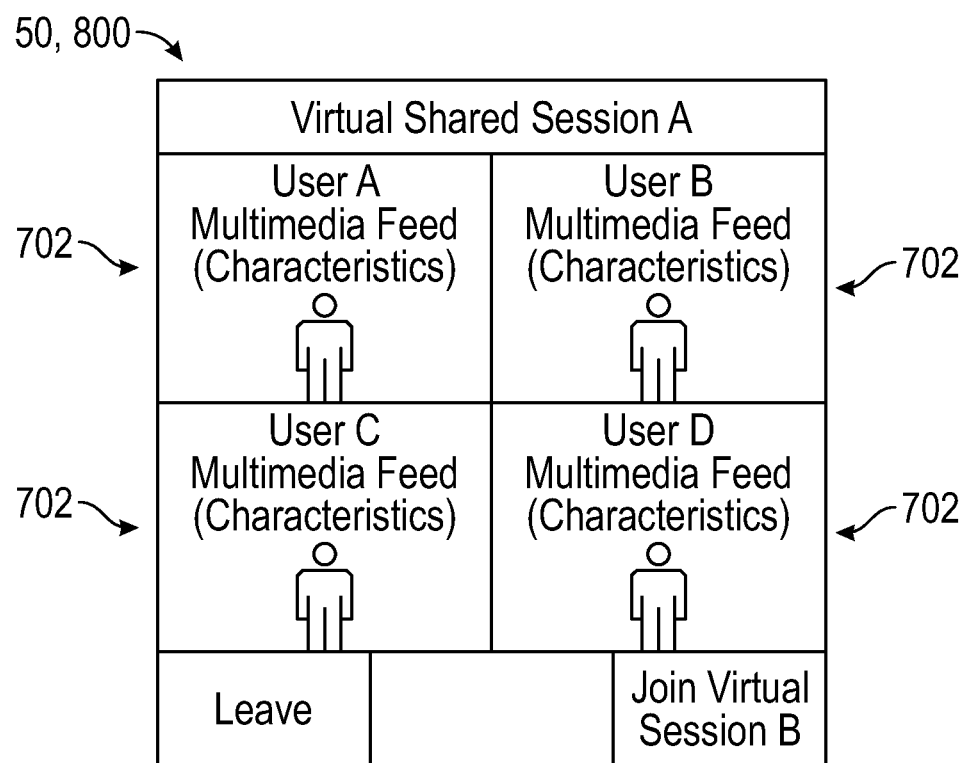

FIGS. 13A-B show an embodiment of a user classifying for two cohorts and enabling the user to select a virtual shared session to join according to the present disclosure. Referring to FIG. 13A, a user may have characteristics that match to more than one cohort. For example, the user may have a particular performance rating that matches with cohort A and a particular age that matches with cohort B. Accordingly, the overview display 800 presented on the patient interface 50 includes the following statement "USER A: you have been matched with two cohorts and virtual shared sessions. Please select from the following virtual shared sessions: Virtual Shared Session A (Cohort A); Virtual Shared Session B (Cohort B). A user may be enabled to use an input peripheral (e.g., mouse, keyboard, touchscreen, microphone) to select one of the virtual shared sessions. As depicted by circle 1300, the user A selected to join virtual shared session A using the input peripheral.

Accordingly, the server 30 may cause user A to be entered into virtual shared session A. In some embodiments, the selection may cause virtual shared session A to be established. In some embodiments, virtual shared session A may not have started yet and user A may be placed into a waiting lobby, or virtual shared session A previously started and user A may join a running virtual shared session.

FIG. 13B shows virtual shared session A established on the user A's patient interface 50. The overview display 800 presents multimedia feeds 702 from other users who are participating in virtual shared session A. The other users are associated with characteristics pertaining to cohort A. As depicted, there is no healthcare professional's multimedia feed present in virtual shared session A, and thus the virtual shared session A is user-led. As depicted, various graphical elements may be presented on the overview display 800. For example, a graphical element representing an option to leave the virtual shared session A is presented, and a graphical element representing an option to join another virtual shared session (e.g., virtual shared session B) with which user A matched. If user A uses an input peripheral to select the graphical element to "Join Virtual Shared Session B", virtual shared session A may be terminated by disconnecting the computing device of user A from the computing devices of the other users (B, C, and D) in virtual shared session A. Further, virtual shared session B may be established on user's A computing device.

Figure 14:
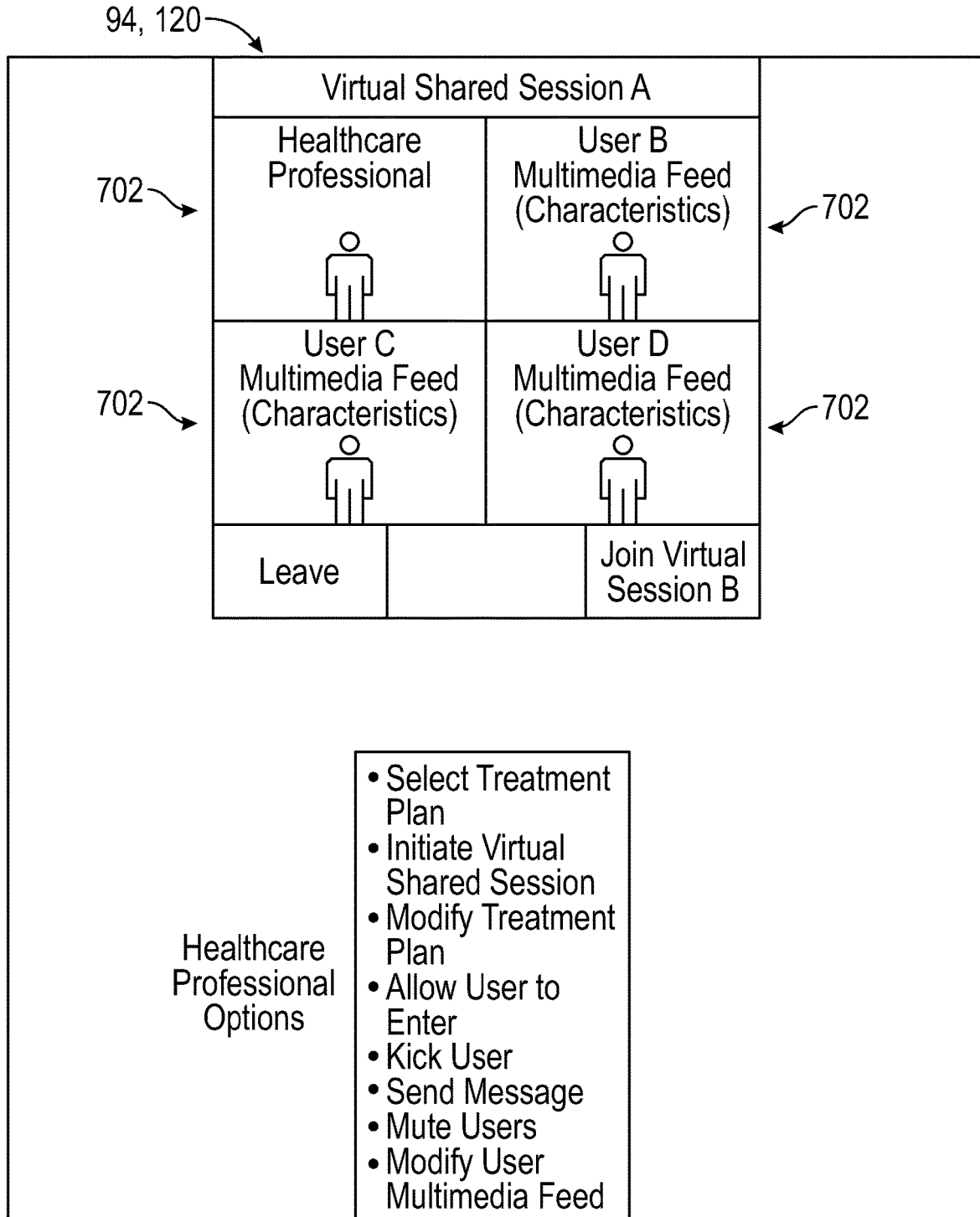
FIG. 14 shows an embodiment of an overview display of an assistant interface presenting a virtual shared session that includes users assigned to a particular cohort according to the present disclosure.

FIG. 14 shows an embodiment of an overview display 120 of an assistant interface 94 presenting a virtual shared session A that includes users assigned to a particular cohort according to the present disclosure. As depicted, the virtual shared session A includes multimedia feeds for the healthcare professional, user B, user C, and user D. The healthcare professional may be enabled to view the characteristics of the users B, C, and D, as depicted. In some embodiments, only the healthcare professional's instance of the virtual shared session A may be granted the ability to receive output or operate to view the users' characteristics, and the instances of the virtual shared session A established on the computing devices of the users may be blocked from presenting the users' characteristics.

Figure 15:
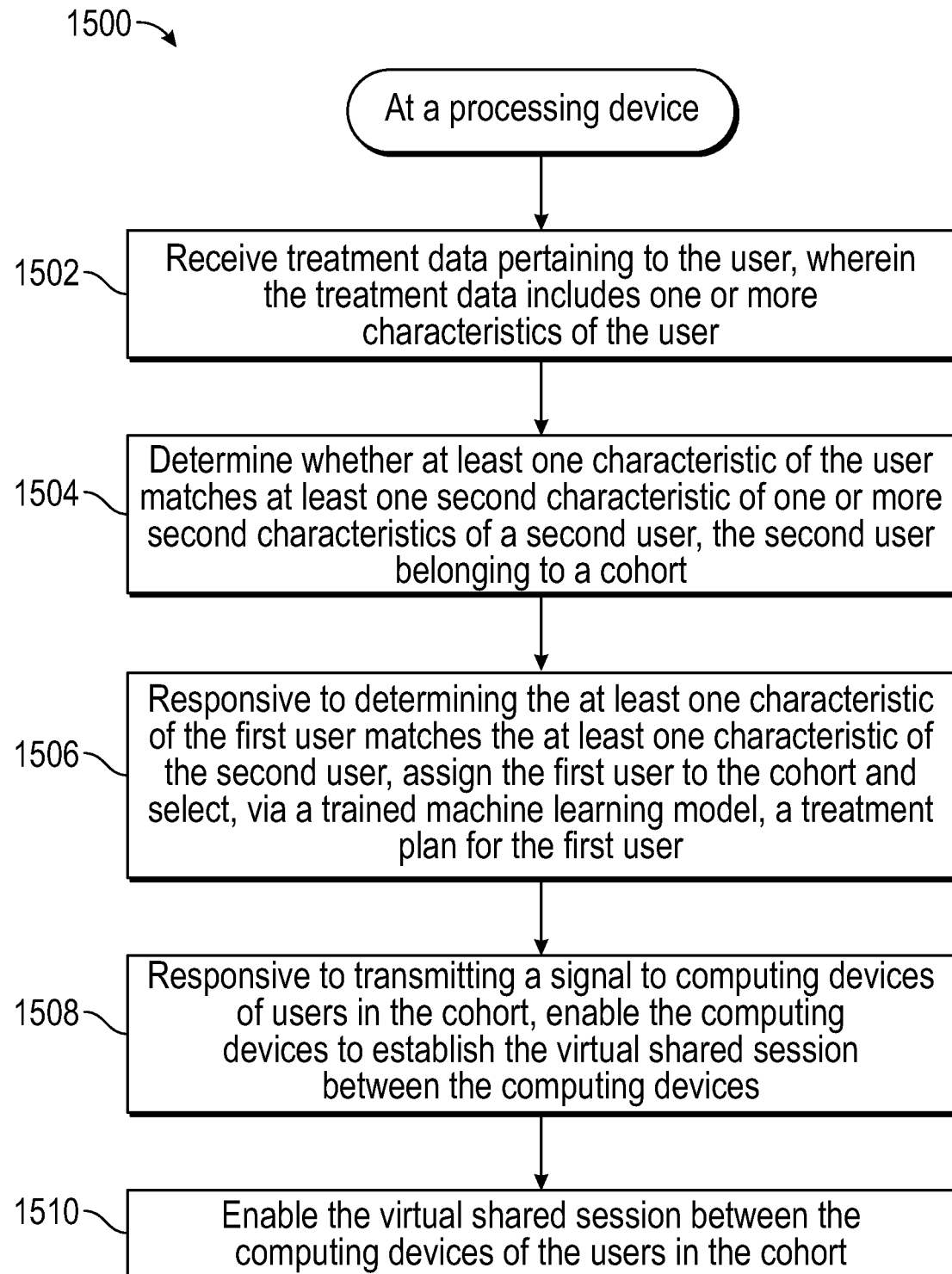
FIG. 15 shows an example embodiment of a method for assigning a user to a cohort and establishing a virtual shared session between computing devices of the users in the cohort according to the present disclosure.

FIG. 15 shows an example embodiment of a method 1500 for assigning a user to a cohort and establishing a virtual shared session between computing devices of the users in the cohort according to the present disclosure. Method 1500 includes operations performed by processors of a computing device (e.g., any component of FIG. 1, such as server 30 executing the artificial intelligence engine 11). In some embodiments, one or more operations of the method 1500 are implemented in computer instructions stored on a memory device and executed by a processing device. The method 1500 may be performed in the same or a similar manner as described above in regard to method 1100. The operations of the method 1500 may be performed in some combination with any of the operations of any of the methods described herein.

At 1502, the processing device may receive treatment data pertaining to the user. The treatment data includes one or more characteristics of the user. The one or more characteristics of the user may be any suitable characteristic as described herein. In some embodiments, the one or more characteristics may pertain to a performance rating, a fitness rating, a rehabilitation rating, a prehabilitation rating, an exercise rating, an athleticism rating, a competition level rating, a credit rating, a personality assessment, a personality inventory, or some combination thereof. The ratings may be determined based on historical records pertaining to the user's performance, exercise, rehabilitation state, winning record of a game or games, losing record of a game or games, a personality test, an electronic medical record (e.g., medical history), a credit score, a fitness assessment test, a blood test, or the like.

At 1504, the processing device may determine whether at least one characteristic of the one or more characteristics of the user matches at least one second characteristic of one or more second characteristics of a second user. The second user may belong to a particular cohort of users having particular characteristics. The computing devices of users in the cohort may include at least a computing device of the first user and a computing device of the second user. In some embodiments, the first and second users are patients, while in other embodiments, the first user is a patient and the second user is a healthcare professional, the first and second users are participants, the first and second users are volunteers, or the first and second users are members of a gym.

At 1506, responsive to determining the at least one characteristic of the first user matches the at least one second characteristic of the second user, the processing device may assign the first user to the cohort and select, via one or more machine learning models 13, a treatment plan for the first user.

At 1508, responsive to transmitting a signal to computing devices of users in the cohort, the processing device may enable the computing devices to establish the virtual shared session between the computing devices of the users in the cohort. The processing device may enable the computing devices by configuring a port, disabling a firewall, authorizing credentials, authorizing an Internet Protocol address, performing an authorization process (e.g., handshake using encryption such as public-private key encryption, OAuth, or the like), or the like.

At 1510, the processing device may enable the virtual shared session between the computing devices of the users in the cohort. The virtual shared session may enable communication between the computing devices of the users in the cohort, wherein the communication comprises video, audio, haptic feedback, text, biometric data, multimedia, or some combination thereof.

In some embodiments, while the first user uses a first treatment apparatus and a second user uses a second treatment apparatus, the processing device may control, based on the treatment plan and during the virtual shared session, the first treatment apparatus and the second treatment apparatus. In some embodiments, the one or more machine learning models 13 may be trained to transmit signals, including control instructions, to the first and second treatment apparatuses. The signals may be received by respective processors of the first and second treatment apparatuses, and the processors may execute the control instructions to modify an operating parameter of the treatment apparatuses to comply with an aspect of the treatment plan. The operating parameter may cause a portion (e.g., pedal) of the treatment apparatus 70 to adjust its range of motion, the motor to increase a speed of the pedals or provide more resistance, etc. The treatment apparatus 70 may be related to mental, neurological, cardiological, and the like.

Figure 16:
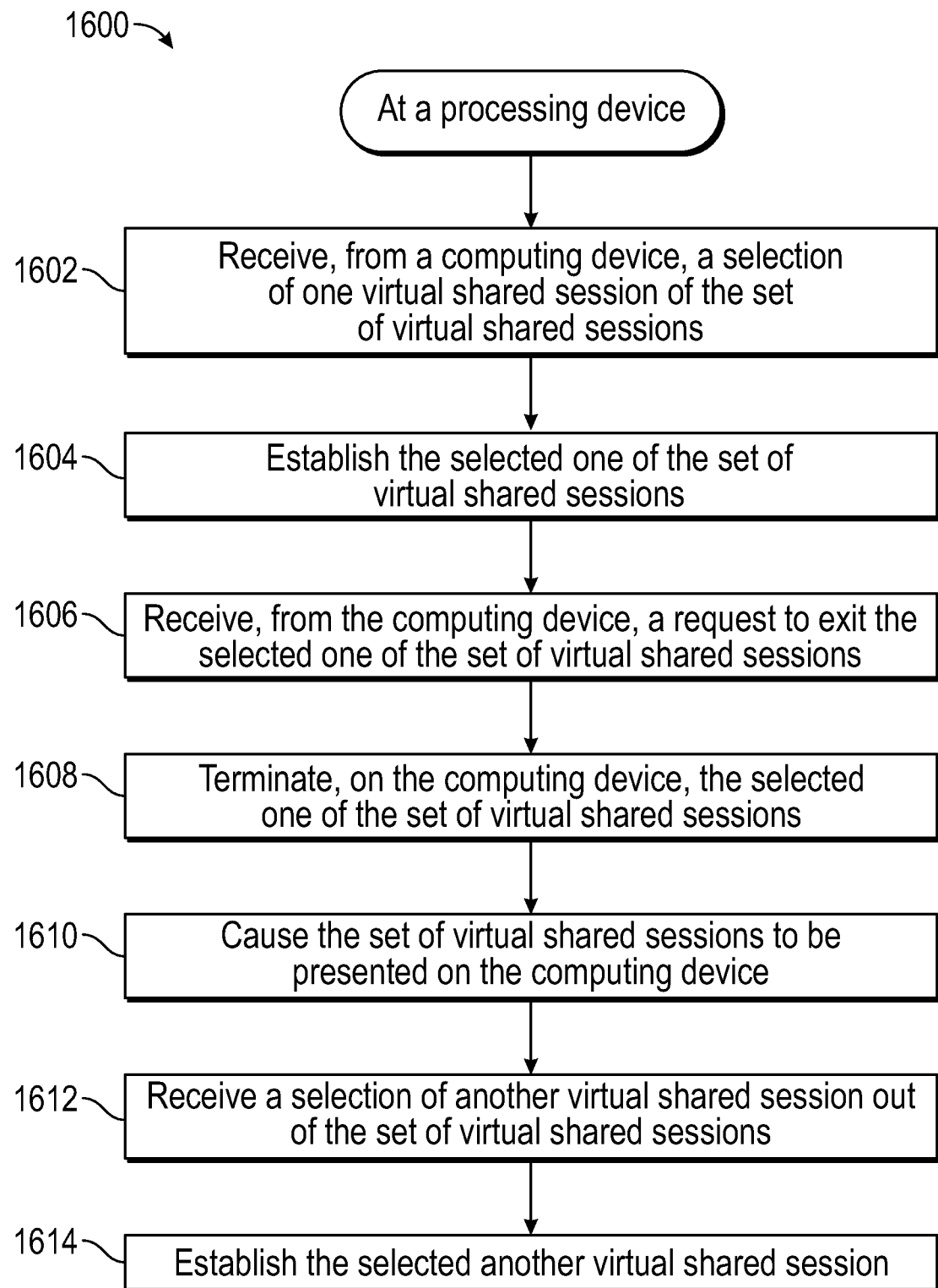
FIG. 16 shows an example embodiment of a method for enabling a user to switch virtual shared sessions according to the present disclosure.

FIG. 16 shows an example embodiment of a method 1600 for enabling a user to switch virtual shared sessions according to the present disclosure. Method 1600 includes operations performed by processors of a computing device (e.g., any component of FIG. 1, such as server 30 executing the artificial intelligence engine 11). In some embodiments, one or more operations of the method 1600 are implemented in computer instructions stored on a memory device and executed by a processing device. The method 1600 may be performed in the same or a similar manner as described above in regard to method 1100. The operations of the method 1600 may be performed in some combination with any of the operations of any of the methods described herein.

Prior to the method 1600 beginning, a user may be assigned to a set of cohorts instead of just one cohort and the user's computing device may present a set of virtual shared sessions associated with the set of cohorts. At 1602, the processing device may receive, from a computing device, a selection of one or more virtual shared sessions out of the set of virtual shared sessions.

At 1604, the processing device may establish the selected one of the plurality of virtual shared sessions. At 1606, the processing device may receive, from the computing device, a request to exit the selected one of the set of virtual shared sessions. At 1608, the processing device may terminate, on the computing device, the selected one of the set of virtual shared sessions. At 1610, the processing device may cause the set of virtual shared sessions to be presented on the computing device. At 1612, the processing device may receive a selection of another virtual shared session out of the set of virtual shared sessions. At 1614, the processing device may establish the selected another virtual shared session.

In some embodiments, as described below with reference to FIG. 17, a healthcare professional may be presented with recommended treatment plans during a telemedicine session (e.g., virtual shared session), and the healthcare professional may select one or more treatments plans to implement for the users participating in the virtual shared session.

Figure 17:
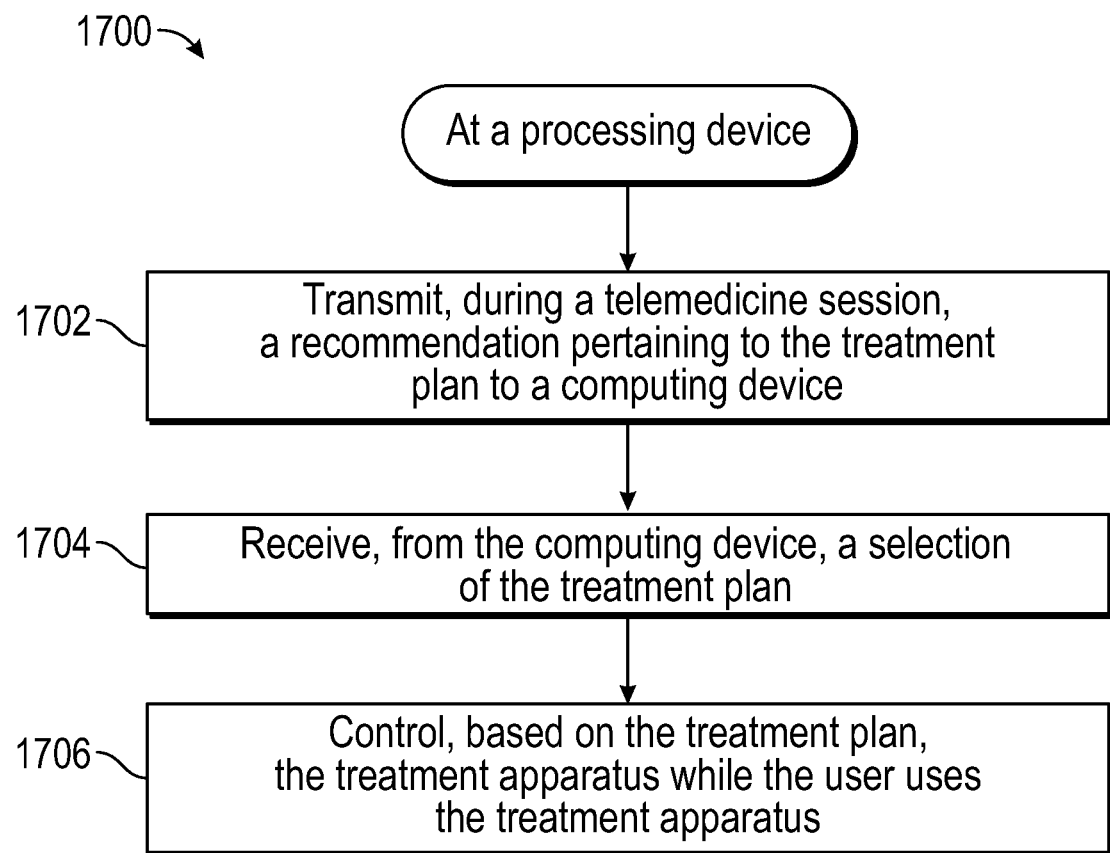
FIG. 17 shows an example embodiment of a method for controlling a treatment apparatus based on a selected treatment plan according to the present disclosure.

FIG. 17 shows an example embodiment of a method 1700 for controlling, based on a treatment plan, a treatment apparatus 70 while a user uses the treatment apparatus 70, according to some embodiments. Method 1700 includes operations performed by processors of a computing device (e.g., any component of FIG. 1, such as server 30 executing the artificial intelligence engine 11). In some embodiments, one or more operations of the method 1700 are implemented in computer instructions stored on a memory device and executed by a processing device. The method 1700 may be performed in the same or a similar manner as described above in regard to method 1100. The operations of the method 1700 may be performed in some combination with any of the operations of any of the methods described herein.

At 1702, the processing device may transmit, during a telemedicine or telehealth session, a recommendation pertaining to a treatment plan to a computing device (e.g., patient interface 50, assistant interface 94, or any suitable interface described herein). The recommendation may be presented on a display screen of the computing device in real-time (e.g., less than 2 seconds) in a portion of the display screen while another portion of the display screen presents video of a user (e.g., patient, healthcare professional, or any suitable user). The recommendation may also be presented on a display screen of the computing device in near time (e.g., preferably more than or equal to 2 seconds and less than or equal to 10 seconds) or with a suitable time delay necessary for the user of the display screen to be able to observe the display screen.

At 1704, the processing device may receive, from the computing device, a selection of the treatment plan. The user (e.g., patient, healthcare professional, assistant, etc.) may use any suitable input peripheral (e.g., mouse, keyboard, microphone, touchpad, etc.) to select the recommended treatment plan. The computing device may transmit the selection to the processing device of the server 30, which is configured to receive the selection. There may any suitable number of treatment plans presented on the display screen. Each of the treatment plans recommended may provide different results and the healthcare professional may consult, during the telemedicine session, with the user, to discuss which result the user desires. In some embodiments, the recommended treatment plans may only be presented on the computing device of the healthcare professional and not on the computing device of the user (patient interface 50). In some embodiments, the healthcare professional may choose an option presented on the assistant interface 94. The option may cause the treatment plans to be transmitted to the patient interface 50 for presentation. In this way, during the telemedicine session, the healthcare professional and the user may view the treatment plans at the same time in real-time or in near real-time, which may provide for an enhanced user experience for the patient and/or healthcare professional using the computing device.

After the selection of the treatment plan is received at the server 30, at 1706, while the user uses the treatment apparatus 70, the processing device may control, based on the selected treatment plan, the treatment apparatus 70. In some embodiments, controlling the treatment apparatus 70 may include the server 30 generating and transmitting control instructions to the treatment apparatus 70. In some embodiments, controlling the treatment apparatus 70 may include the server 30 generating and transmitting control instructions to the patient interface 50, and the patient interface 50 may transmit the control instructions to the treatment apparatus 70. The control instructions may cause an operating parameter (e.g., speed, orientation, required force, range of motion of pedals, etc.) to be dynamically changed according to the treatment plan (e.g., a range of motion may be changed to a certain setting based on the user achieving a certain range of motion for a certain period of time). The operating parameter may be dynamically changed while the patient uses the treatment apparatus 70 to perform an exercise. In some embodiments, during a telemedicine session between the patient interface 50 and the assistant interface 94, the operating parameter may be dynamically changed in real-time or near real-time.

Figure 18:
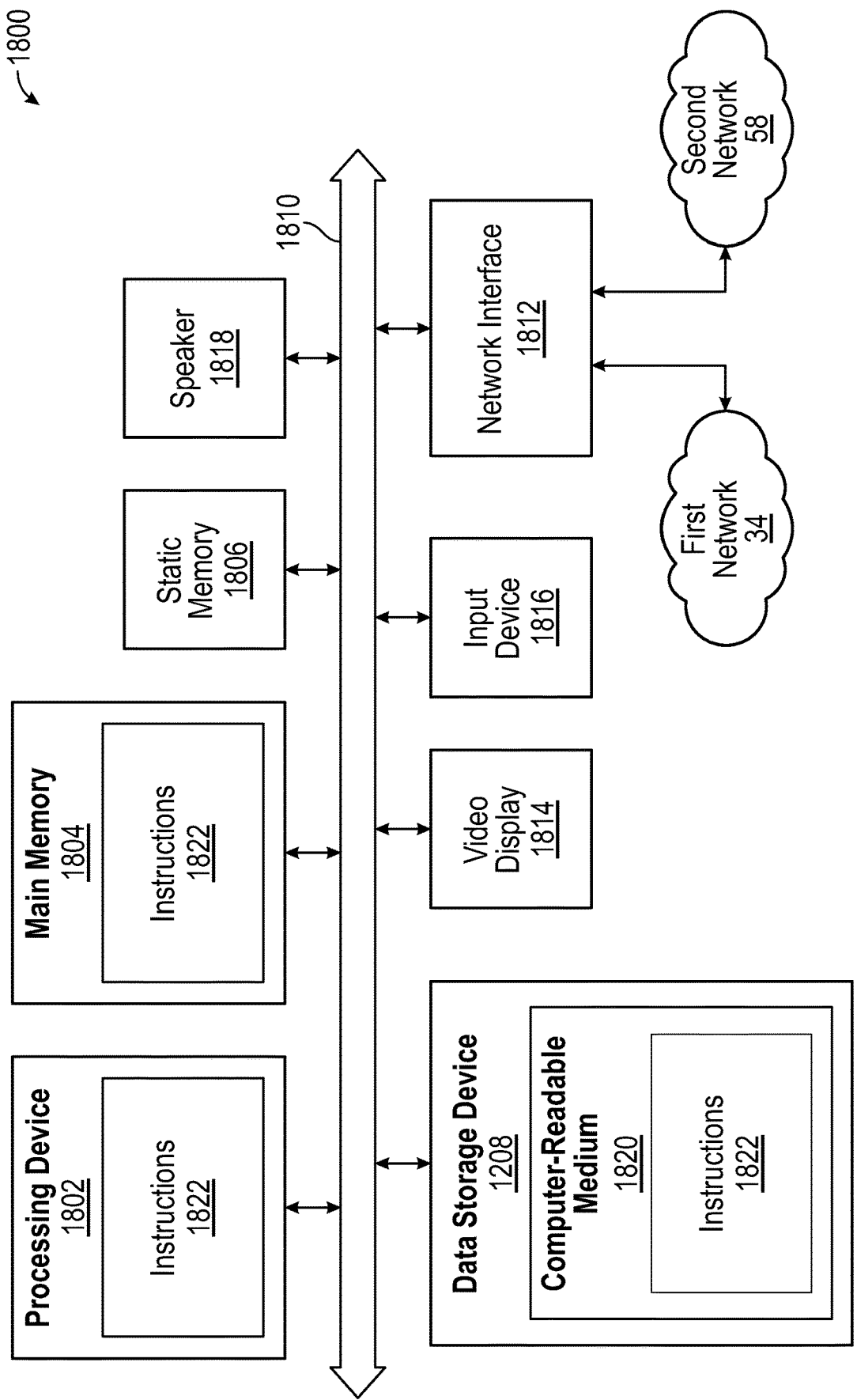
FIG. 18 shows an example computer system according to the present disclosure.

FIG. 18 shows an example computer system 1800 which can perform any one or more of the methods described herein, in accordance with one or more aspects of the present disclosure. In one example, computer system 1800 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1800 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1800 includes a processing device 1802, a main memory 1804 (e.g., read-only memory (ROM), flash memory, solid state drives (SSDs), dynamic random access memory (DRAM) such as synchronous DRAM (SDRAM)), a static memory 1806 (e.g., flash memory, solid state drives (SSDs), static random access memory (SRAM)), and a data storage device 1808, which communicate with each other via a bus 1810.

Processing device 1802 represents one or more general-purpose processing devices such as a microprocessor, central processing unit, or the like. More particularly, the processing device 1802 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1800 may further include a network interface device 1812. The computer system 1800 also may include a video display 1814 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1816 (e.g., a keyboard and/or a mouse or a gaming-like control), and one or more speakers 1818 (e.g., a speaker). In one illustrative example, the video display 1814 and the input device(s) 1816 may be combined into a single component or device (e.g., an LCD touch screen).

The data storage device 1816 may include a computer-readable medium 1820 on which the instructions 1822 embodying any one or more of the methods, operations, or functions described herein is stored. The instructions 1822 may also reside, completely or at least partially, within the main memory 1804 and/or within the processing device 1802 during execution thereof by the computer system 1800. As such, the main memory 1804 and the processing device 1802 also constitute computer-readable media. The instructions 1822 may further be transmitted or received over a network via the network interface device 1812.

While the computer-readable storage medium 1820 is shown in the illustrative examples to be a single medium, the term "computer-readable storage medium" should be taken to include a single medium or multiple media (e.g., a centralized or distributed database, and/or associated caches and servers) that store the one or more sets of instructions.

The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A computer-implemented method comprising:
receiving a plurality of first characteristics pertaining to a plurality of users;
initiating a virtual shared session on a plurality of computing devices associated with a plurality of users, wherein the virtual shared session comprises at least a plurality of multimedia feeds, and each multimedia feed of the plurality of multimedia feeds is associated with one or more of the users of the plurality of users; and
during the virtual shared session, presenting a first layout comprising the plurality of multimedia feeds, the plurality of first characteristics, or some combination thereof.

Clause 2. The computer-implemented method of any clause herein, further comprising:
receiving a plurality of second characteristics pertaining to the plurality of users; and
rearranging, based on the plurality of second characteristics, the first layout to create a second layout comprising the plurality of multimedia feeds, the plurality of second characteristics, or some combination thereof.

Clause 3. The computer-implemented method of any clause herein, wherein the rearranging is performed during the virtual shared session.

Clause 4. The computer-implemented method of any clause herein, wherein the first layout and the second layout are determined by one or more machine learning models trained to determine layouts, wherein the one or more machine learning models are trained using user characteristic data, vital sign data, user performance data, compliance data, therapy data, ratings data, or some combination thereof.

Clause 5. The computer-implemented method of any clause herein, further comprising causing the presentation of the first layout and second layout:
on a plurality of displays of the plurality of computing devices,
as a plurality of projections on a plurality of surfaces,
inside one or more virtual reality or augmented reality headsets, or
some combination thereof.

Clause 6. The computer-implemented method of any clause herein, wherein the projection arises out of one or more virtual reality or augmented reality devices.

Clause 7. The computer-implemented method of any clause herein, wherein a respective subset of the plurality of first characteristics is associated with a user of the plurality of users, and the respective subset is presented relative to the multimedia feed associated with the user of the plurality of users.

Clause 8. The computer-implemented method of any clause herein, wherein either or both of the plurality of first characteristics and the plurality of second characteristics are received from a plurality of sources comprising a treatment apparatus, a sensor, a camera, a computing device, biometric methods, a database, or some combination thereof.

Clause 9. The computer-implemented method of any clause herein, further comprising, based on at least a portion of the plurality of first characteristics, using one or more machine learning models to provide a notification to a computing device of the plurality of computing devices, wherein the notification includes text, audio, video, haptic feedback, or some combination thereof.

Clause 10. The computer-implemented method of any clause herein, wherein the plurality of users comprise a healthcare professional, a patient, a participant, a volunteer, or some combination thereof.

Clause 11. The computer-implemented method of any clause herein, wherein the virtual shared session pertains to rehabilitative therapy, prehabilitative therapy, strength training, mental health therapy, an exercise session, or some combination thereof.

Clause 12. The computer-implemented method of any clause herein, further comprising controlling, based on either or both of the plurality of first characteristics and the plurality of second characteristics, at least one treatment apparatus used by at least one user of the plurality of users, wherein the controlling is performed during the virtual shared session.

Clause 13. The computer-implemented method of any clause herein, further comprising:
determining a plurality of ratings for the plurality of users, wherein the plurality of ratings is based on electronic medical records, measurement data, the plurality of first characteristics, the plurality of second characteristics, or some combination thereof;
during the virtual shared session, receiving a plurality of third characteristics pertaining to the plurality of users; and
maintaining, based on the plurality of ratings and the plurality of third characteristics, the second layout.

Clause 14. The computer-implemented method of any clause herein, further comprising communicating the plurality of ratings and the plurality of third characteristics to one or more users, wherein the communication is made private such that only the rated user is made aware of that user's ratings.

Clause 15. The computer-implemented method of any clause herein, wherein a healthcare professional associated with the rated user is further made aware of that user's ratings.

Clause 16. The computer-implemented method of any clause herein, wherein the virtual shared session comprises a telemedicine session and at least one of the plurality of computing devices is associated with a healthcare professional.

Clause 17. A non-transitory, computer-readable medium storing instructions that, when executed, cause a processing device to:
receive a plurality of first characteristics pertaining to a plurality of users;
initiate a virtual shared session on a plurality of computing devices associated with a plurality of users, wherein the virtual shared session comprises at least a plurality of multimedia feeds, and each multimedia feed of the plurality of multimedia feeds is associated with one or more of the users of the plurality of users; and
during the virtual shared session, present a first layout comprising the plurality of multimedia feeds, the plurality of first characteristics, or some combination thereof.

Clause 18. The computer-readable medium of any clause herein, wherein the processing device is further to:
receive a plurality of second characteristics pertaining to the plurality of users;
and
rearrange, based on the plurality of second characteristics, the first layout to create a second layout comprising the plurality of multimedia feeds, the plurality of second characteristics, or some combination thereof.

Clause 19. A system comprising:
a memory device storing instructions; and
a processing device communicatively coupled to the memory device, the processing device executes the instructions to:
receive a plurality of first characteristics pertaining to a plurality of users;
initiate a virtual shared session on a plurality of computing devices associated with a plurality of users, wherein the virtual shared session comprises at least a plurality of multimedia feeds, and each multimedia feed of the plurality of multimedia feeds is associated with one or more of the users of the plurality of users; and
during the virtual shared session, present a first layout comprising the plurality of multimedia feeds, the plurality of first characteristics, or some combination thereof.

Clause 20. The system of any clause herein, wherein the processing device is further to:
receive a plurality of second characteristics pertaining to the plurality of users; and
rearrange, based on the plurality of second characteristics, the first layout to create a second layout comprising the plurality of multimedia feeds, the plurality of second characteristics, or some combination thereof.

Clause 21. A computer-implemented method for configuring a virtual shared treatment session to encourage a user compliance with a treatment plan, the method comprising:
receiving treatment data pertaining to the user, wherein the treatment data comprises one or more characteristics of the user;
determining whether at least one characteristic of the one or more characteristics of the user matches at least one second characteristic of one or more second characteristics of a second user, the second user belonging to a cohort;
responsive to determining the at least one characteristic of the first user matches the at least one second characteristic of the second user, assigning the first user to the cohort and selecting, via a trained machine learning model, a treatment plan for the first user;
responsive to transmitting a signal to computing devices of users in the cohort, enabling the computing devices to establish the virtual shared session between the computing devices; and
enabling the virtual shared session between the computing devices of the users in the cohort.

Clause 22. The computer-implemented method of any clause herein, wherein the computing devices of users in the cohort comprise at least a computing device of the first user and a computing device of the second user.

Clause 23. The computer-implemented method of any clause herein, wherein the first user is a patient and the second user is a patient, or the first user is a patient and the second user is a healthcare professional.

Clause 24. The computer-implemented method of any clause herein, wherein the first user is assigned to a plurality of cohorts and presented with a plurality of virtual shared sessions, wherein the method further comprises:
receiving, from a computing device, a selection of one virtual shared session out of the plurality of virtual shared sessions; and
establishing the selected one of the plurality of virtual shared sessions.

Clause 25. The computer-implemented method of any clause herein, further comprising:
receiving, from the computing device, a request to exit the selected one of the plurality of virtual shared sessions;
terminating, on the computing device, the selected one of the plurality of virtual shared sessions;
causing the plurality of virtual shared sessions to be presented on the computing device;
receiving a selection of another virtual shared session out of the plurality of virtual shared sessions; and
establishing the selected another virtual shared session.

Clause 26. The computer-implemented method of any clause herein, wherein the one or more characteristics of the first user and the one or more second characteristics of the second user pertain to a performance rating, a fitness rating, a rehabilitation rating, a prehabilitation rating, an exercise rating, an athleticism rating, a competition level rating, a credit rating, a personality assessment, a personality inventory, or some combination thereof.

Clause 27. The computer-implemented method of any clause herein, further comprising, while the first user uses a first treatment apparatus and a second user uses a second treatment apparatus, controlling, based on the treatment plan and during the virtual shared session, the first treatment apparatus and the second treatment apparatus.

Clause 28. The computer-implemented method of any clause herein, wherein the virtual shared session enables communication between the computing devices of the users in the cohort, wherein the communication comprises video, audio, haptic feedback, text, biometric data, multimedia, or some combination thereof.

Clause 29. A non-transitory, computer-readable medium storing instructions that, when executed, cause a processing device to:
receive treatment data pertaining to the user, wherein the treatment data comprises one or more characteristics of the user;
determine whether at least one characteristic of the one or more characteristics of the user matches at least one second characteristic of one or more second characteristics of a second user, the second user belonging to a cohort;
responsive to determining the at least one characteristic of the first user matches the at least one second characteristic of the second user, assign the first user to the cohort and selecting, via a trained machine learning model, a treatment plan for the first user;
responsive to transmitting a signal to computing devices of users in the cohort, enable the computing devices to establish the virtual shared session between the computing devices; and
enable the virtual shared session between the computing devices of the users in the cohort.

Clause 30. The computer-readable medium of any clause herein, wherein the computing devices of users in the cohort comprise at least a computing device of the first user and a computing device of the second user.

Clause 31. The computer-readable medium of any clause herein, wherein the first user is a patient and the second user is a patient, or the first user is a patient and the second user is a healthcare professional.

Clause 32. The computer-readable medium of any clause herein, wherein the first user is assigned to a plurality of cohorts and presented with a plurality of virtual shared sessions, wherein processing device is further to:
receive, from a computing device, a selection of one virtual shared session out of the plurality of virtual shared sessions; and
establish the selected one of the plurality of virtual shared sessions.

Clause 33. The computer-readable medium of any clause herein, wherein the processing device is further to:
receive, from the computing device, a request to exit the selected one of the plurality of virtual shared sessions;
terminate, on the computing device, the selected one of the plurality of virtual shared sessions;
cause the plurality of virtual shared sessions to be presented on the computing device;
receive a selection of another virtual shared session out of the plurality of virtual shared sessions; and
establish the selected another virtual shared session.

Clause 34. The computer-readable medium of any clause herein, wherein the one or more characteristics of the first user and the one or more second characteristics of the second user pertain to a performance rating, a fitness rating, a rehabilitation rating, a prehabilitation rating, an exercise rating, an athleticism rating, a competition level rating, a credit rating, a personality assessment, a personality inventory, or some combination thereof.

Clause 35. The computer-readable medium of any clause herein, wherein the processing device is further to, while the first user uses a first treatment apparatus and a second user uses a second treatment apparatus, control, based on the treatment plan and during the virtual shared session, the first treatment apparatus and the second treatment apparatus.

Clause 36. The computer-readable medium of any clause herein, wherein the virtual shared session enables communication between the computing devices of the users in the cohort, wherein the communication comprises video, audio, haptic feedback, text, biometric data, multimedia, or some combination thereof.

Clause 37. A system comprising:
a memory device storing instructions;
a processing device communicatively coupled to the memory device, the processing device executes the instructions to:
receive treatment data pertaining to the user, wherein the treatment data comprises one or more characteristics of the user;
determine whether at least one characteristic of the one or more characteristics of the user matches at least one second characteristic of one or more second characteristics of a second user, the second user belonging to a cohort;
responsive to determining the at least one characteristic of the first user matches the at least one second characteristic of the second user, assign the first user to the cohort and selecting, via a trained machine learning model, a treatment plan for the first user;
responsive to transmitting a signal to computing devices of users in the cohort, enable the computing devices to establish the virtual shared session between the computing devices; and
enable the virtual shared session between the computing devices of the users in the cohort.

Clause 38. The system of any clause herein, wherein the computing devices of users in the cohort comprise at least a computing device of the first user and a computing device of the second user.

Clause 39. The system of any clause herein, wherein the first user is a patient and the second user is a patient, or the first user is a patient and the second user is a healthcare professional.

Clause 40. The system of any clause herein, wherein the first user is assigned to a plurality of cohorts and presented with a plurality of virtual shared sessions, wherein processing device is further to:

receive, from a computing device, a selection of one virtual shared session out of the plurality of virtual shared sessions; and
establish the selected one of the plurality of virtual shared sessions.

Clause 41. A computer-implemented system, comprising:
a plurality of treatment apparatuses configured to be manipulated by a plurality of patients while performing an exercise session;
a plurality of patient interfaces associated with the plurality of patients; and
a server computing device configured to:
receive a plurality of first characteristics pertaining to the plurality of patients;
initiate a virtual shared session on the plurality of patient interfaces associated with the plurality of patients, wherein the virtual shared session comprises at least a plurality of multimedia feeds, and each multimedia feed of the plurality of multimedia feeds is associated with one or more of the patients of the plurality of patients; and
during the virtual shared session, present a first layout comprising the plurality of multimedia feeds, the plurality of first characteristics, or some combination thereof.

Clause 42. The computer-implemented system of any clause herein, wherein the server computing device is further to:
receive a plurality of second characteristics pertaining to the plurality of patients;
and
rearrange, based on the plurality of second characteristics, the first layout to create a second layout comprising the plurality of multimedia feeds, the plurality of second characteristics, or some combination thereof.

Clause 43. The computer-implemented system of any clause herein, wherein the rearranging is performed during the virtual shared session.

Clause 44. The computer-implemented system of clause herein, wherein the first layout and the second layout are determined by one or more machine learning models trained to determine layouts, wherein the one or more machine learning models are trained using user characteristic data, vital sign data, user performance data, compliance data, therapy data, ratings data, or some combination thereof.

Clause 45. The computer-implemented system of any clause herein, wherein the server computing device is further to:
cause the presentation of the first layout and second layout:
on a plurality of displays of the plurality of patient interfaces,
as a plurality of projections on a plurality of surfaces,
inside one or more virtual reality or augmented reality headsets, or
some combination thereof.

Clause 46. The computer-implemented system of any clause herein, wherein the projection arises out of one or more virtual reality or augmented reality devices.

Clause 47. The computer-implemented system of any clause herein, wherein a respective subset of the plurality of first characteristics is associated with a patient of the plurality of patients, and the respective subset is presented relative to the multimedia feed associated with the user of the plurality of patients.

Clause 48. The computer-implemented system of any clause herein, wherein either or both of the plurality of first characteristics and the plurality of second characteristics are received from a plurality of sources comprising the plurality of treatment apparatuses, a sensor, a camera, a computing device, biometric methods, a database, or some combination thereof.

Clause 49. The computer-implemented system of any clause herein, further comprising, based on at least a portion of the plurality of first characteristics, using one or more machine learning models to provide a notification to a patient interface of the plurality of patient interfaces, wherein the notification includes text, audio, video, haptic feedback, or some combination thereof.

Clause 50. The computer-implemented method of any clause herein, wherein the plurality of patients comprise a healthcare professional, a patient, a participant, a volunteer, or some combination thereof.

Clause 51. A computer-implemented system, comprising:
a treatment apparatus configured to be manipulated by a user while performing an exercise session;
patient interfaces associated with users; and
a server computing device for configuring a virtual shared treatment session to encourage user compliance with a treatment plan associated with the exercise session, wherein the server computing device is configured to:
receive treatment data pertaining to the user, wherein the treatment data comprises one or more characteristics of the user;
determine whether at least one characteristic of the one or more characteristics of the user matches at least one second characteristic of one or more second characteristics of a second user, the second user belonging to a cohort;
responsive to determining the at least one characteristic of the user matches the at least one second characteristic of the second user, assign the user to the cohort and select, via a trained machine learning model, a treatment plan for the user;
responsive to transmitting a signal to the patient interfaces of users in the cohort, enable the patient interfaces to establish the virtual shared session between the patient interfaces; and
enable the virtual shared session between the patient interfaces.

Clause 52. The computer-implemented system of any clause herein, wherein the patient interfaces in the cohort comprise at least a patient interface of the user and a patient interface of the second user.

Clause 53. The computer-implemented system of any clause herein, wherein the user is a patient and the second user is a patient, or the user is a patient and the second user is a healthcare professional.

Clause 54. The computer-implemented system of any clause herein, wherein the user is assigned to a plurality of cohorts and presented with a plurality of virtual shared sessions, wherein the server computing device is further to:
receive, from a computing device, a selection of one virtual shared session out of the plurality of virtual shared sessions; and
establish the selected one of the plurality of virtual shared sessions.

Clause 55. The computer-implemented system of any clause herein, wherein the server computing device is further to:
receive, from a patient interface of the user, a request to exit the selected one of the plurality of virtual shared sessions;
terminate, on the patient interface, the selected one of the plurality of virtual shared sessions;
cause the plurality of virtual shared sessions to be presented on the patient interface;
receive a selection of another virtual shared session out of the plurality of virtual shared sessions; and
establish the selected another virtual shared session.

Clause 56. The computer-implemented system of any clause herein, wherein the one or more characteristics of the user and the one or more second characteristics of the second user pertain to a performance rating, a fitness rating, a rehabilitation rating, a prehabilitation rating, an exercise rating, an athleticism rating, a competition level rating, a credit rating, a personality assessment, a personality inventory, or some combination thereof.

Clause 57. The computer-implemented system of any clause herein, wherein the server computing device is further to, while the first user uses the treatment apparatus and a second user uses a second treatment apparatus, controlling, based on the treatment plan and during the virtual shared session, the treatment apparatus and the second treatment apparatus.

Clause 58. The computer-implemented method of any clause herein, wherein the virtual shared session enables communication between the patient interfaces of the users in the cohort, wherein the communication comprises video, audio, haptic feedback, text, biometric data, multimedia, or some combination thereof.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:
1. A computer-implemented system, comprising:
a treatment apparatus configured to be manipulated by a user while the user performs an exercise session;
patient interfaces associated with users; and
a server computing device for configuring a virtual shared treatment session to encourage user compliance with a treatment plan associated with the exercise session, wherein the server computing device is configured to:
receive treatment data pertaining to the user, wherein the treatment data comprises one or more characteristics of the user;
determine whether at least one characteristic of the one or more characteristics of the user matches at least one second characteristic of one or more second characteristics of a second user, the second user belonging to a cohort;
responsive to determining the at least one characteristic of the user matches the at least one second characteristic of the second user, assign the user to the cohort and select, via a trained machine learning model, a treatment plan for the user;
responsive to transmitting a signal to the patient interfaces of users in the cohort, enable the patient interfaces to establish the virtual shared session between the patient interfaces; and
enable the virtual shared session between the patient interfaces.
2. The computer-implemented system of claim 1, wherein the patient interfaces in the cohort comprise at least a patient interface of the user and a patient interface of the second user.

3. The computer-implemented system of claim 1, wherein the user is a patient and the second user is a patient, or the user is a patient and the second user is a healthcare professional.

4. The computer-implemented system of claim 1, wherein the user is assigned to a plurality of cohorts and presented with a plurality of virtual shared sessions, wherein the server computing device is further to:
receive, from a computing device, a selection of one virtual shared session out of the plurality of virtual shared sessions; and
establish the selected one of the plurality of virtual shared sessions.

5. The computer-implemented system of claim 4, wherein the server computing device is further to:
receive, from a patient interface of the user, a request to exit the selected one of the plurality of virtual shared sessions;
terminate, on the patient interface, the selected one of the plurality of virtual shared sessions;
cause the plurality of virtual shared sessions to be presented on the patient interface;
receive a selection of a different virtual shared session out of the plurality of virtual shared sessions; and
establish the selected different virtual shared session.

6. The computer-implemented system of claim 1, wherein the one or more characteristics of the user and the one or more second characteristics of the second user pertain to a performance rating, a fitness rating, a rehabilitation rating, a prehabilitation rating, an exercise rating, an athleticism rating, a competition level rating, a credit rating, a personality assessment, a personality inventory, or some combination thereof.

7. The computer-implemented system of claim 1, wherein, while the first user uses the treatment apparatus and a second user uses a second treatment apparatus, the server computing device is further to control, based on the treatment plan and during the virtual shared session, the treatment apparatus and the second treatment apparatus.

8. The computer-implemented method of claim 1, wherein the virtual shared session enables communication between the patient interfaces of the users in the cohort, wherein the communication comprises video, audio, haptic feedback, text, biometric data, multimedia, gestures, or some combination thereof.

9. A computer-implemented method for configuring a virtual shared treatment session to encourage a user compliance with a treatment plan, the method comprising:
receiving treatment data pertaining to the user, wherein the treatment data comprises one or more characteristics of the user;
determining whether at least one characteristic of the one or more characteristics of the user matches at least one second characteristic of one or more second characteristics of a second user, the second user belonging to a cohort;
responsive to determining the at least one characteristic of the first user matches the at least one second characteristic of the second user, assigning the first user to the cohort and selecting, via a trained machine learning model, a treatment plan for the first user;
responsive to transmitting a signal to computing devices of users in the cohort, enabling the computing devices to establish the virtual shared session between the computing devices; and
enabling the virtual shared session between the computing devices of the users in the cohort.

10. The computer-implemented method of claim 9, wherein the computing devices of users in the cohort comprise at least a computing device of the first user and a computing device of the second user.

11. The computer-implemented method of claim 9, wherein the first user is a patient and the second user is a patient, or the first user is a patient and the second user is a healthcare professional.

12. The computer-implemented method of claim 9, wherein the first user is assigned to a plurality of cohorts and presented with a plurality of virtual shared sessions, wherein the method further comprises:
receiving, from a computing device, a selection of one virtual shared session out of the plurality of virtual shared sessions; and
establishing the selected one of the plurality of virtual shared sessions.

13. The computer-implemented method of claim 12, further comprising:
receiving, from the computing device, a request to exit the selected one of the plurality of virtual shared sessions;
terminating, on the computing device, the selected one of the plurality of virtual shared sessions;
causing the plurality of virtual shared sessions to be presented on the computing device;
receiving a selection of a different virtual shared session out of the plurality of virtual shared sessions; and
establishing the selected different virtual shared session.

14. The computer-implemented method of claim 9, wherein the one or more characteristics of the first user and the one or more second characteristics of the second user pertain to a performance rating, a fitness rating, a rehabilitation rating, a prehabilitation rating, an exercise rating, an athleticism rating, a competition level rating, a credit rating, a personality assessment, a personality inventory, or some combination thereof.

15. The computer-implemented method of claim 9, further comprising, while the first user uses a first treatment apparatus and a second user uses a second treatment apparatus, controlling, based on the treatment plan and during the virtual shared session, the first treatment apparatus and the second treatment apparatus.

16. The computer-implemented method of claim 9, wherein the virtual shared session enables communication between the computing devices of the users in the cohort, wherein the communication comprises video, audio, haptic feedback, text, biometric data, multimedia, gestures, or some combination thereof.

17. A non-transitory, computer-readable medium storing instructions that, when executed, cause a processing device to:
receive treatment data pertaining to the user, wherein the treatment data comprises one or more characteristics of the user;
determine whether at least one characteristic of the one or more characteristics of the user matches at least one second characteristic of one or more second characteristics of a second user, the second user belonging to a cohort;
responsive to determining the at least one characteristic of the first user matches the at least one second characteristic of the second user, assign the first user to the cohort and selecting, via a trained machine learning model, a treatment plan for the first user;

responsive to transmitting a signal to computing devices of users in the cohort, enable the computing devices to establish the virtual shared session between the computing devices; and enable the virtual shared session between the computing devices of the users in the cohort.

18. The computer-readable medium of claim 17, wherein the computing devices of users in the cohort comprise at least a computing device of the first user and a computing device of the second user.

19. The computer-readable medium of claim 17, wherein the first user is a patient and the second user is a patient, or the first user is a patient and the second user is a healthcare professional.

20. The computer-readable medium of claim 17, wherein the first user is assigned to a plurality of cohorts and presented with a plurality of virtual shared sessions, wherein processing device is further to:

receive, from a computing device, a selection of one virtual shared session out of the plurality of virtual shared sessions; and establish the selected one of the plurality of virtual shared sessions.

21. The computer-readable medium of claim 20, wherein the processing device is further to:

receive, from the computing device, a request to exit the selected one of the plurality of virtual shared sessions;

terminate, on the computing device, the selected one of the plurality of virtual shared sessions;

cause the plurality of virtual shared sessions to be presented on the computing device;

receive a selection of a different virtual shared session out of the plurality of virtual shared sessions; and establish the selected different virtual shared session.

22. The computer-readable medium of claim 17, wherein the one or more characteristics of the first user and the one or more second characteristics of the second user pertain to a performance rating, a fitness rating, a rehabilitation rating, a prehabilitation rating, an exercise rating, an athleticism rating, a competition level rating, a credit rating, a personality assessment, a personality inventory, or some combination thereof.

23. The computer-readable medium of claim 17, wherein the processing device is further to, while the first user uses a first treatment apparatus and a second user uses a second treatment apparatus, control, based on the treatment plan and during the virtual shared session, the first treatment apparatus and the second treatment apparatus.

24. The computer-readable medium of claim 17, wherein the virtual shared session enables communication between the computing devices of the users in the cohort, wherein the communication comprises video, audio, haptic feedback, text, biometric data, multimedia, gestures, or some combination thereof.

25. A system comprising:

a memory device storing instructions;

a processing device communicatively coupled to the memory device, the processing device executes the instructions to:

receive treatment data pertaining to the user, wherein the treatment data comprises one or more characteristics of the user;

determine whether at least one characteristic of the one or more characteristics of the user matches at least one second characteristic of one or more second characteristics of a second user, the second user belonging to a cohort;

responsive to determining the at least one characteristic of the first user matches the at least one second characteristic of the second user, assign the first user to the cohort and selecting, via a trained machine learning model, a treatment plan for the first user;

responsive to transmitting a signal to computing devices of users in the cohort, enable the computing devices to establish the virtual shared session between the computing devices; and enable the virtual shared session between the computing devices of the users in the cohort.

26. The system of claim 25, wherein the computing devices of users in the cohort comprise at least a computing device of the first user and a computing device of the second user.

27. The system of claim 25, wherein the first user is a patient and the second user is a patient, or the first user is a patient and the second user is a healthcare professional.

28. The system of claim 25, wherein the first user is assigned to a plurality of cohorts and presented with a plurality of virtual shared sessions, wherein processing device is further to:

receive, from a computing device, a selection of one virtual shared session out of the plurality of virtual shared sessions; and establish the selected one of the plurality of virtual shared sessions.

29. The system of claim 25, wherein the processing device is further to, while the first user uses a first treatment apparatus and a second user uses a second treatment apparatus, control, based on the treatment plan and during the virtual shared session, the first treatment apparatus and the second treatment apparatus.

30. The system of claim 25, wherein the virtual shared session enables communication between the computing devices of the users in the cohort, wherein the communication comprises video, audio, haptic feedback, text, biometric data, multimedia, or some combination thereof.

* * * * *